United States Patent [19]

Fujino et al.

[11] 4,073,890
[45] * Feb. 14, 1978

[54] NOVEL POLYPEPTIDES

[75] Inventors: Masahiko Fujino, Takarazuka; Mitsuhiro Wakimasu; Shigehisa Taketomi, both of Suita; Eiichiro Ishikawa, Nishinomiya, all of Japan

[73] Assignee: Takeda Chemical Industries, Ltd., Osaka, Japan

[*] Notice: The portion of the term of this patent subsequent to Jan. 4, 1994, has been disclaimed.

[21] Appl. No.: 726,052

[22] Filed: Sept. 23, 1976

Related U.S. Application Data

[62] Division of Ser. No. 560,092, March 19, 1975, Pat. No. 4,001,199.

[30] Foreign Application Priority Data

Mar. 26, 1974  Japan .................................. 49-34161
Jan. 24, 1975  Japan .................................. 50-10878

[51] Int. Cl.$^2$ .................... A61K 37/00; C07C 103/52
[52] U.S. Cl. .............................. 424/177; 260/112.5 R
[58] Field of Search ................. 260/112.5 R; 424/177

[56] References Cited

U.S. PATENT DOCUMENTS 3,778,426  12/1973  Najjar ........................... 260/112.5 R
3,891,616  6/1975  Onedetti ....................... 260/112.5 R
4,001,199  1/1977  Fujino et al. ................. 260/112.5 R Primary Examiner—Delbert R. Phillips
Attorney, Agent, or Firm—Wenderoth, Lind & Ponack

[57]  ABSTRACT

Novel polypeptides of the formula $R_1$—Arg—$R_2$—Phe—Phe—$R_3$ wherein $R_1$ is hydrogen, or a basic or neutral amino acid residue, $R_2$ is a neutral amino acid residue and $R_3$ is $NH_2$, Tyr—$NH_2$, a residue of tyrosyl peptides consisting of 1 to 5 amino acid residues or amides of the tyrosyl peptides, provided that when $R_1$ is hydrogen, $R_2$ is Pro, are effectively used for treatment of insufficiency of carbohydrate metabolism and of lipid metabolism, especially for the treatment of diabetes by not only parenteral administration but also oral administration.

21 Claims, No Drawings

NOVEL POLYPEPTIDES

This application is a divisional application of application Ser. No. 560,092 filed Mar. 19, 1975 now U.S. Pat. No. 4,001,199.

The present invention relates to novel polypeptides of the formula $$R_1\text{-Arg-}R_2\text{-Phe-Phe-}R_3 \qquad (I)$$

wherein $R_1$ is hydrogen, or a basic or neutral amino acid residue, $R_2$ is a neutral amino acid residue and $R_3$ is $NH_2$, Tyr-$NH_2$ or a residue of tyrosyl peptides consisting of 1 to 5 amino acid residues or a residue of amides of the tyrosyl peptides, provided that when $R_1$ is hydrogen, $R_2$ is Pro.

The polypeptides (I) are effectively used for treatment of insufficiency of carbohydrate metabolism and of lipid metabolism, especially for the treatment of diabetes mellitus.

Through the present specification and the claims, abbreviations are used for designating amino acids, peptides and their activating or protective groups, and activating and protecting agents of amino acids or peptides according to those of IUPAC-IUB Commission on Biological Nomenclature or to those commonly used in this particular field of the art. Examples of the abbreviations are as follows:

α-Abu: α-Aminobutyric acid
γ-Abu: γ-Aminobutyric acid
ε-Acap: ε-Aminocaproic acid
Ala: Alanine
β-Ala: β-Alanine
Arg: Arginine
δ-Aval: δ-Aminovaleric acid
α,γ-Dab: α,γ-Diaminobutyric acid
Gly: Glycine
His: Histidine
Leu: Leucine
Lys: Lysine
Nle: Norleucine
Phe: Phenylalanine
Pro: Proline
Sar: Sarcosine
Ser: Serine
Thr: Threonine
Tyr: Tyrosine
Val: Valine
Aoc: t-Amyloxycarbonyl
Bzl: Benzyl ether
DCC: N,N'-Dicyclohexylcarbodiimide
HONB: N-Hydroxy-5-norbornene-2,3-dicarboximide
OBzl: Benzyl ester
ODNP: 2,4-Dinitrophenyl ester
OEt: Ethyl ester
ONB: HONB ester
Opcp: Pentachlorophenyl ester
Osu: N-Hydroxysuccinimide ester
OtBu: t-Butyl ester
Tos: Tosyl
Z: Benzyloxycarbonyl In the present specification and the claims, in a case where there are optical isomers with respect to amino acids, the amino acids mean each of the optical isomers or racemic compounds unless otherwise specifically designated. When $R_1$ is hydrogen, the group $R_1$-Arg means the following arginyl group:

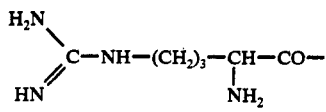

The term "amino acid residue" means a group being capable of forming a peptide bond, i.e. a group of the amino acid being deprived of either one of or both hydrogen of its amino or imino group and hydroxy of its carboxyl group.

The basic or neutral amino acids represented by $R_1$ have preferably 2 to 10 carbon atoms. The basic amino acids are exemplified by such α-amino acids as α,β-diaminopropionic acid, α,γ-diaminobutyric acid, arginine, lysine or histidine. The neutral amino acids represented by $R_1$ are exemplified by such α-amino acids as glycine, alanine, serine, threonine, α-aminobutyric acid, proline, leucine, isoleucine, norleucine phenylalanine and tyrosine, and other amino acids such as β-alanine, γ-aminobutyric acid, δ-aminovaleric acid and ε-aminocaproic acid. Where there are optical isomers with those amino acids represented by $R_1$, the amino acids may be any of the optical isomers and racemic compounds. Among amino acids corresponding to $R_1$, β-alanine is preferable for the intended use.

The neutral amino acids represented by $R_2$ have preferably 2 to 10 carbon atoms and are exemplified by glycine, alanine, β-alanine, sarcosine, serine, proline, valine, leucine, isoleucine, phenylalanine and tyrosine.

Among amino acids corresponding to $R_2$, glycine and proline are preferable for the intended use. In a case where $R_2$ is a residue of proline, the intended use is attained even when $R_1$ is hydrogen.

Amino acids which can constitute the tyrosyl peptides or its amides have preferably 2 to 10 carbon atoms each and are exemplified by glycine, alanine, serine, threonine, valine, proline, leucine, isoleucine, lysine, phenylalanine and tyrosine. Those amino acids are conjugated in any sequence to form the tyrosyl peptides or their amides comprising 1 to 5 amino acid residues. Following are the examples of such tyrosyl peptides, and their respective amides are similarly exemplifiable as the tyrosyl peptide amides.

(1) Tyr—Gly—OH
(2) Tyr—Ala—Gly—OH
(3) Tyr—Leu—Ala—Gly—OH
(4) Tyr—Leu—Gly—Val—Ala—OH
(5) Tyr—Thr—Pro—Ser—Phe—OH
(6) Tyr—Thr—Pro—Lys—Ala—OH
(7) Tyr—Thr—Pro—Lys—Thr—OH
(8) Tyr—Ser—Pro—Arg—Gly—OH
(9) Tyr—Pro—Ile—OH
(10) Tyr—Leu—Leu—Leu—OH
(11) Tyr—Gly—Gly—Gly—Gly—OH
(12) Tyr—Ala—Ala—Ala—Ala—OH
(13) Tyr—Thr—Pro—Lys—OH

Among amino acids and tyrosyl peptides and their amides, Tyr-$NH_2$ is preferable for the intended use as well as for their industrial production.

As to the amino acids represented by $R_2$ or constituting the $R_3$ group, in a case where there are optical isomers, the amino acids may be any of the optical isomers and racemic compounds. As to the amino acid residues constituting the polypeptides (I) except those represented by $R_1$, in a case where there are optical isomers, L-amino acid residues are preferable owing to their lower toxicity.

In accordance with the process of the present invention, the polypeptides (I) are produced by condensing an amino acid corresponding to $R_1$ or arginine where $R_1$ is hydrogen, or a peptide fragment of the polypeptide (I) having the amino acid residue $R_1$ or arginyl group when $R_1$ is hydrogen as its N-terminal amino acid with the remaining fragment of the polypeptide (I), and each of the starting materials may be protected at its amino or carboxyl group which should not be involved in the contemplated condensation and may be activated at its amino or carboxyl group which is involved in the contemplated condensation, and removing the protective groups from the resultant product if any.

The present condensation is carried out according to per se conventional condensation for formation of peptide linkages.

The present condensation is carried out between any optional positions of the polypeptides (I) to form the contemplated peptide or amide linkages. Condensation between the 3rd amino acid component corresponding to $R_2$ and the 4th amino acid component corresponding to phenylalanine may be preferable for the industrial production of the polypeptides (I).

Like known polypeptide compounds, the polypeptides of this invention may be synthesized from material amino acids being components of the product polypeptide through the repetition of condensation reactions. And, usually, the last step of the synthesis is the condensation between two components, i.e. peptide and terminal amino acid or two peptides. These two components are the starting materials of the last step of the condensations to synthesizing the product. These starting materials or final intermediates may be obtained via any of per se conventional process for peptide synthesis.

The starting materials in the present process are exemplified by amino acids per se of N-terminal amino acids of the polypeptides (I), and peptide fragments consisting of the N-terminal amino acids to which each of the amino acids is consecutively attached in accordance with the amino acid sequence of the polypeptides (I). Mating starting materials are fragments of the remainder of the polypeptides (I) except for the said starting materials.

Combinations of the starting materials and their mating starting materials are principally exemplified in the following table.

Table 1

| Starting Materials | |
|---|---|
| $R_1$-OH | H-Arg-$R_2$-Phe-Phe-$R_3$ |
| $R_1$-Arg-OH | H-$R_2$-Phe-Phe-$R_3$ |
| $R_1$-Arg-$R_2$-OH | H-Phe-Phe-$R_3$ |
| $R_1$-Arg-$R_2$-Phe-OH | H-Phe-$R_3$ |
| $R_1$-Arg-$R_2$-Phe-Phe-OH | H-$R_3$ |
| $R_1$Arg-$R_2$-Phe-Phe-OH | H-Tyr-NH$_2$ |
| $R_1$-Arg-$R_2$-Phe-Phe-Tyr-OH | NH$_3$ |

The condensation reaction according to this invention can be carried out by condensing means known for the formation of peptide linkages. Among such means of condensation are DCC/HONB process (Belgian Pat. No. 796,399), the azide process, chloride process, acid anhydride process, mixed acid anhydride process, DCC process, active ester process, Woodward reagent K process, carbodiimidazole process, oxidation-reduction process and others (The Peptides, Vol. 1 (1966), Schroder and Lubke, Academic Press, New York, U.S.A.).

Prior to the condensation reaction, one may protect the carboxyl and amino groups which should not be involved in the contemplated reaction or activate the carboxyl or/and amino groups which will take part in the contemplated reaction, by means which are known per se. The carboxyl groups in the starting material which should not be involved in the contemplated reaction may be protected in the form of metal salts (e.g. sodium and potassium salts) or esters (e.g. methyl, ethyl, benzyl, p-nitrobenzyl, t-butyl or t-amyl esters).

Protective groups for amino groups in the starting materials may be any of conventional protecting groups for amino groups in peptide synthesis, e.g. benzyloxycarbonyl, t-butoxycarbonyl, t-amyloxycarbonyl, isobornyloxycarbonyl, etc. These protective groups may be used for protecting imino group of proline. The imidazole function of histidine may be protected with any of conventional protecting group such as benzyl, tosyl, 2,4-dinitrophenol, t-butoxycarbonyl or carbobenzoxy. The hydroxyl group of serine, tyrosine or threonine may be protected with a conventional protective group such as benzyl, t-butyl and other ether-forming groups. The guanidino group of arginine may be protected with such groups as nitro, tosyl, carbobenzoxy, isobornyloxycarbonyl or adamantyloxycarbonyl. As examples of activated carboxyl groups in starting materials, there may be mentioned the corresponding acid anhydride, azide, active esters (esters with alcohols (e.g. pentachlorophenyl, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide or N-hydroxybenztriazole), etc. The activated amino groups in the starting materials may for example be the corresponding phosphoric acid amide.

The following table shows some exemplary combinations of such forms of carboxyl and amino groups in materials (A) and (B).

Table 2

| Exemplary Combinations | Starting Materials | | | |
|---|---|---|---|---|
| | (A) | | (B) | |
| | COOH | NH$_2$ | COOH | NH$_2$ |
| 1* | Free | Protected | Protected | Free |
| 2 | Activated | Protected | Free | Free |
| 3 | Free | Protected | Protected | Activated |

(Note)
In the case designated by an asterisk*, a dehydrating agent (e.g. a carbodiimide reagent such as dicyclohexyl-carbodiimide) is preferably present in the reaction system.

The present condensation may be conducted in the presence of a solvent. The solvent can be selected from those known to be useful for peptide condensation reactions. Thus, anhydrous or aqueous dimethylformamide, dimethylsulfoxide, pyridine, chloroform, dioxane, dichloromethane, tetrahydrofuran and suitable mixtures of such solvents may be mentioned by way of example.

The reaction temperature is selected from within the range known to be employable for reactions leading to the formation of peptide bonds, i.e. normally within the range of about $-20°$ C to about 30° C. Further, the precursor materials (protected peptides) of the contemplated compounds according to this invention may also be easily prepared by solid-phase synthetic processes.

After the contemplated condensation reaction has been completed, if the product carries protective groups, they can be removed by routine procedures.

Among such routine procedures are catalytic reduction in the presence of a catalyst such as palladium black, palladium-on-carbon, platinum or the like, solvolysis by means of hydrogen fluoride, trifluoroacetic acid or the like, and reduction with metallic sodium in liquid ammonia.

The peptide (I) thus produced can be recovered from the reaction product mixture by procedures known for the recovery of peptides, e.g. by extraction, distribution, column chromatography, etc.

The present reaction may be carried out by per se conventional solid phase method.

The polypeptide (I) may also be recovered in the form of a salt or metal complex compound.

As acids which are able to form salts with the polypeptide (I), there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, citric acid, succinic acid, maleic acid, fumaric acid, anthranylic acid, cinnamic acid, naphthalenesulfonic acid or sulfanylic acid, for instance.

The metals which are able to form metal complex compounds with the polypeptide (I) include, among others, zinc, nickel, cobalt, copper and iron. Such a metal complex compound can be produced by conventional procedures, for example, by reacting the polypeptide (I) with the hydroxide or oxide of a metal of the above-mentioned variety at pH about 6 to 8.

The polypeptides (I) of the present invention have activity of lowering high content of glucose in blood and urine to a normal level by not only parenteral administration but also oral administration. The polypeptides (I) have a surprisingly specific activity of not reducing a normal level of glucose in blood and urine, which is far superior to insulin causing hypoglycemia. The polypeptides (I) are low toxic and administered safely. The polypeptides (I) have also activity of promoting lipid metabolism. Having such specific utility, the polypeptides (I) are effectively administered to human beings and other animals such as rats or mice by oral or parenteral route for treating insufficiency of carbohydrate metabolism and lipid metabolism, especially for treatment of diabetes or hypercholesteremia without causing any undesirable effect. The polypeptides (I) can be administered as such, or in any pharmaceutical forms, such as tblets, pellets, granules, powder, liquid or injection which can be prepared by per se conventional procedures.

Examples of recipe of pharmaceutical compositions are as follows.

| Injection | |
|---|---|
| Polypeptide (I) of the formula β-Ala-L-Arg-L-Pro-L-Phe-L-Phe-L-Tyr-NH$_2$ diacetate | 50 mg. |
| Physiological saline | 2.0 ml. |
| Powder | |
| Polypeptide (I) of the formula β-Ala-L-Arg-Gly-L-Phe-L-Phe-L-Tyr-NH$_2$dicitrate | 30 mg. |
| Starch | 200 mg. |

While daily dose of the polypeptides (I) are variable depending upon disease, severity of the disease, age of host, etc., it is usually selected from about 50 μg. to about 100 mg./kg. body weight.

Pharmacological Experiment on Amelioration of Diabetes by the Polypeptides (I)

Eight-week old females of genetically diabetic mice (KKA$^y$ or yellow KK mice) were kept individually in metal cages to collect urine. Three groups of mice were orally administered the polypeptide (I) of the formula β-Ala-L-Arg-Gly-L-Phe-L-Phe-L-Tyr-NH$_2$ (Compound A) at three different dosages (1, 10 and 100 mg/kg/day). The treatment procedure is depicted in the Table 3. The control group was given saline solution. Every 4 days, plasma and urinary glucose were determined by glucose oxidase method (Huggett, A. St. G. and Nixon, D. A., "Lamcet" volume II, pages 368–370(1957)).

Results are cited in the Table 3. In the control group, the plasma glucose level and urinary glucose excreted for 24 hours were very high throughout the period of the experiment. By contrast, either plasma glucose or urinary glucose of groups treated with the polypeptide was gradually decreasing during the treatment. A dose-dependent fashion could be observed in these antidiabetic effects. In the post-treatment phase, both glucose levels were increasing in three treated groups. However, a dose-dependency was observed in the persistence of the antidiabetic effects after withdrawal.

From these findings, it can be concluded that the polypeptide ameliorates diabetes of these mice. Treatment Procedure

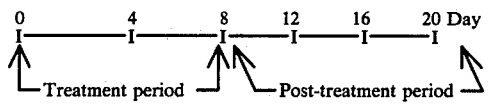

PG: plasma glucose (mg./100 ml.) UG: urinary glucose (g/day)
*significant vs the saline group (p< 0.05)
**significant vs the saline group (p< 0.01)

Table 3

| Drug | No. of Mice | Pre-treatment | | Drug-treatment (day) | | | | | | Post-treatment (day) | | | |
|---|---|---|---|---|---|---|---|---|---|---|---|---|---|
| | | | | 4th | | 8th | | 12th | | 16th | | 20th | |
| | | PG | UG | PG | UG | PG | UG | PG | UG | PG | UG | PG | UG |
| Saline | 5 | 445±39 | 0.560±0.072 | 483±35 | 0.484±0.051 | 528±45 | 0.635±0.072 | 497±76 | 0.557±0.152 | 447±22 | 0.462±0.070 | 513±53 | 0.486±0.052 |
| Compound A 1 mg/kg/day | 5 | 457±43 | 0.595±0.081 | 352±36 | 0.299±0.092 | 343±17** | 0.213±0.079** | 370±40 | 0.190±0.010 | 469±22 | 0.451±0.091 | 523±58 | 0.450±0.056 |
| Compound A 10mg/kg/day | 3 | 458±43 | 0.571±0.075 | 433±78 | 0.160±0.061** | 338±35* | 0.0786±0.0346** | 354±25 | 0.0858±0.0472* | 396±7 | 0.238±0.099 | 513±101 | 0.478±0.022 |
| Compound A 100mg/kg/day | 5 | 455±14 | 0.582±0.068 | 344±27* | 0.0743±0.0279** | 254±41** | 0.0446±0.0200** | 232±19** | 0.0466±0.0220* | 339±44 | 0.0750±0.0188** | 457±51 | 0.250±0.045** |

In all the working Examples, in a case where there are optical isomers with respect to amino acids, the amino acids are in the form of L-configuration unless otherwise specifically designated.

EXAMPLE 1

Production of Arg-Pro-Phe-Phe-Tyr-NH$_2$ (a) Preparation of Z-Arg(NO$_2$)-Pro-Phe-Phe-Tyr-NH$_2$ In 50 ml. of DMF(dimethylformamide) was dissolved 10.0 g. of z-Phe-Phe-Tyr-NH$_2$ and catalytic reduction was carried out with Pd-black as a catalyst for 10 hours. The catalyst was filtered off and while the filtrate was cooled with ice, 7.37 g. of Z-Arg(NO$_2$)-Pro-OH and 3.53 g. of HONB were added.

This procedure was further followed by the addition of 4.06 g. of DCC and the mixture was stirred for 16 hours. The formed DC (dicyclohexyl-) urea was filtered off and the DMF was distilled off under reduced pressure. To the residue was added 200 ml. of ethyl acetate and the resulting powder was collected by filtration. The powder was purified by reprecipitation from DMF-methanol-water. Yield 14.5 g. (95.6 %); melting point: 100°-103° C; $[\alpha]_D^{24} - 29.7°$ (c=0.55 %, DMF).

Elemental analysis: for C$_{46}$H$_{54}$O$_{10}$N$_{10}$.H$_2$O
Calcd. C, 59.73; H, 6.10; N, 15.11
Found C, 59.51; H, 6.06; N, 14.90

(b) Preparation of Arg-Pro-Phe-Phe-Tyr-NH$_2$ in 30 ml. of acetic acid was dissolved 500 mg. of Z-Arg(NO$_2$)-Pro-Phe-Phe-Tyr-NH$_2$, and catalytic reduction was carried out with Pd-black as a catalyst for 20 hours. The catalyst was filtered off and the filtrate was concentrated to dryness under reduced pressure. The residue was dissolved in 50 ml. of water and, after the small amounts of insolubles were filtered off, the filtrate was lyophilized. The product was dissolved in 5 ml. of water and the solution was applied on a column (1.8 × 9 cm) of carboxymethyl-sephadex. Gradient elution was carried out with 0.1M aqueous ammonium acetate (400 ml.) and 1M aqueous ammonium acetate (400 ml.). The fractions from 250 ml. to 370 ml. were pooled and lyophilized to yield 250 mg. (52.3 %) of a white fluffy product. $[\alpha]_D^{24} - 41.9°$ (c=0.47 %, water)

Amino acid analysis (hydrolysis with HCl): Arg,1.00; Pro 1.05; Tyr, 0.91; Phe, 1.96; (peptide content 86.5 %)

Elemental analysis, for C$_{38}$H$_{49}$O$_6$N$_9$.2C$_2$H$_4$O$_2$.2H$_2$O
Calcd. C, 57.06; H, 6.96; N, 14.26 Found C, 56.76; H, 6.98; N, 14.28

EXAMPLE 2

Production of Gly-Arg-Pro-Phe-Phe-Tyr-NH$_2$ (a) Preparation of Z-Gly-Arg-Pro-Phe-Phe-Tyr-NH$^2$ In 30 ml. of acetic acid was dissolved 800 mg. of Z-Arg(NO$_2$)-Pro-Phe-Phe-Tyr-NH$_2$ and catalytic reduction was carried out with Pd-black as a catalyst for 8 hours. The catalyst was filtered off and the filtrate was concentrated to dryness under reduced pressure. The residue was dissolved in 20 ml. of water and lyophilized.

The resulting powder was dissolved in 10 ml. of DMF and 147 mg. of p-toluenesulfonic acid monohydrate was added. To the mixture was added 349 mg. of Z-Gly-ONB, followed by stirring for 10 hours. The DMF was distilled off under reduuced pressure and 50 ml. of ethyl acetate was added. The resulting power was collected by filtration. Yield 858 mg. (89.5 %); melting point: 119°-121° C; $[\alpha]_D^{23} -26.7°$ (c=0.96%, DMF).

elemental analysis; for C$_{48}$H$_{58}$O$_9$N$_{10}$.C$_7$H$_8$O$_3$S.H$_2$O
Calcd. C, 59.55; H, 6.18; N, 12.63; S, 2.89 Found C, 59.45; H, 6.08; N, 12.37; S, 2.76

(b) Preparation of Gly-Arg-Pro-Phe-Phe-Tyr-NH$_2$

In 30 ml. of acetic acid was dissolved 500 mg. of Z-Gly-Arg-Pro-Phe-Phe-Tyr-NH$_2$ p-toluenesulfonate and catalytic reduction was carried out with Pd-black as a catalyst for 5 hours. The catalyst was filtered off and the solvent was distilled off under reduced pressure. The residue was dissolved in 20 ml. of water and the solution was subjected to ion-exchange chromatography on a column of Amberlite IRA 410 (acetate-form) (Strongly basic anion exchange resin of Rohm & Haas Co. Ltd., U.S.A.). The eluate was lyophilized and the resulting powder was dissolved in 5 ml. of water. The solution was applied on a column (2.6 × 23 cm) of carboxymethyl-cellulose and elution was carried out by the gradient method using 0.005M to 0.2M aqueous ammonium acetate (700 ml. each). The fractions from 840 ml. to 970 ml. were pooled and lyophilized. Yield 270 mg. (63.6 %); $[\alpha]_D^{22} - 62.0°$ (c=0.46 %, water)

Elemental analysis, for C$_{40}$H$_{52}$O$_7$N$_{10}$.2C$_2$H$_4$O$_2$.2H$_2$O
Calcd. C, 56.15; H, 6.86; N, 14.89 Found C, 55.99; H, 6.92; N, 14.77

Amino acid analysis: Arg, 0.94; Pro, 1.06; Gly, 1.00; Tyr, 0.94; Phe, 2.03 (peptide content: 83.2%)

EXAMPLE 3

Production of γ-Abu-Arg-Pro-Phe-Phe-Tyr-NH$_2$

The procedure of Example 2 was followed except that Z-γ-Abu-ONB was used in place of Z-Gly-ONB to obtain 324 mg. of the above-indicated compound. $[\alpha]_D^{22} - 58.7°$(c=0.45 %, water)

Elemental analysis, for C$_{42}$H$_{56}$O$_7$N$_{10}$.2C$_2$H$_4$O$_2$.3H$_2$O
Calcd. C, 55.97; H, 7.15; N, 14.19 Found C, 56.14; H, 7.36; N, 13.92

Amino acid analysis: Arg, 1.00; Pro, 1.08; Tyr, 0.97; Phe, 2.13 (peptide content: 80.8%)

EXAMPLE 4

Production of ε-Acap-Arg-Pro-Phe-Phe-Tyr-NH$_2$ (a) Preparation of Zε-Acap-Arg-Pro-Phe-Phe-Tyr-NH$_2$ In 10 ml. of DMF was dissolved 250 mg. of Z-ε-AcapOH and, under cooling with ice, 186 mg. of HONB and 214 mg. of DCC were added. The mixture was stirred for 16 hours and the formed DC-urea was filtered off. The filtrate was added to a DMF solution of H-Arg-Pro-Phe-Phe-Tyr-NH$_2$ p-toluenesulfonate which had been prepared in the same manner as Example 2-a). The mixture was stirred for 12 hours and the DMF was distilled off under reduced pressure. To the residue was added 30 ml. of ethyl acetate and the resulting powder was collected by filtration. Yield 810 mg. (79.1 %); melting point: 90-92° C, $[\alpha]_D^{23} - 30.3°$(c=1.07 %, DMF)

Elemental analysis, for C$_{52}$H$_{66}$O$_9$N$_{10}$.C$_7$H$_8$O$_3$S.2H$_2$O
Calcd. C, 59.88; H, 6.65; N, 11.84; S, 2.80 Found C, 59.81; H, 6.75; N, 11.80; S, 3.00

(b) Preparation of ε-Acap-Arg-Pro-Phe-Phe-Tyr-NH$_2$ 500 mg. of the Z-derivative prepared in a) was treated in the same manner as Example 2-b) to obtain 316 mg. of the above-indicated compound. $[\alpha]_D^{23} - 58.9°$(c=0.55 %, water) Amino acid analysis: Arg, 1.02; Pro, 1.03; Tyr, 0.92; Phe, 2.13; ε-Acap(not determined)(peptide content: 81.5 %)

EXAMPLE 5

Production of Lys-Arg-Pro-Phe-Phe-Tyr-NH$_2$ (a) Preparation of di-Z-Lys-Arg-Pro-Phe-Phe-Tyr-NH$_2$ The proceduure of Example 4-a) was repeated except that 390 mg. of di-Z-Lys-Oh was used in place of Z-ε-AcapOH to obtain 932 mg. of the above-indicated compound. melting point: 103°–105° C; $[\alpha]_D^{23}$ −28.5°(c=1.04 %; DMF)

Elemental analysis, for C$_{60}$H$_{73}$O$_{11}$N$_{11}$.C$_7$H$_8$O$_3$S.2H$_2$O Calcd. C, 60.39; H, 6.43; N, 11.56; S, 2.41 Found C, 60.64; H, 6.21; N, 11.79; S, 2.82

(b) Preparation of Lys-Arg-Pro-Phe-Phe-Tyr-NH$_2$ 500 mg. of the di-Z-derivative prepared in a) was treated in the same manner as Example 2-b) to obtain 336 mg. of the above-indicated compound. $[\alpha]_D^{23}$ −52.6°(c=0.57 %, water) Amino acid analysis: Lys, 1.02; Arg, 0.98; Pro, 1.00; Tyr, 0.94; Phe, 2.04 (peptide content: 91 %)

EXAMPLE 6

Production of α,γ-Dab-Arg-Pro-Phe-Phe-Tyr-NH$_2$

In exactly the same manner as Examples 4 and 5, the above-indicated compound was synthesized from 535 mg. of the di-Z-α,γ-Dab-dicyclohexylamine salt. Yield 325 mg. $[\alpha]_D^{23}$ −58.2°(c=0.50 %, water)

Amino acid analysis: α,γ-Dab, 1.00; Arg, 0.98; Pro, 1.00;

Tyr, 0.87; Phe, 1.96 (peptide content: 84.2 %)

EXAMPLE 7

Production of β-Ala-Arg-Pro-Phe-Phe-Tyr-NH$_2$ (a) Preparation of Z-β-Ala-Arg(NO$_2$)-Pro-OMe To 3.50 g. of Z-Arg(NO$_2$)-Pro-OMe was added 35 ml. of 25 % HBr-acetic acid and the mixture was shaken at room temperature for 35 minutes. To this mixture was added 300 ml. of ethyl ether and the resulting precipitate was collected by filtration, washed with ether and dried.

The powder was dissolved in 20 ml. of DMF and, under cooling with ice, the solution was neutralized with triethylamine. Following the addition of 2.9 g. of Z-β-Ala-ONB, the mixture was stirred for 16 hours.

The DMF was distilled off under pressure and the residue was dissolved in 300 ml. of ethyl acetate. The solution was washed three times with 100 ml. portions of 4 % aqueous sodium hydrogen carbonate. After washing with water, the solution was dried over anhydrous sodium sulfate. The solvent was distilled off under reduced pressure and ethyl ether was added to the residue. The resulting powder was collected by filtration. Yield 3.05 g. (74.3 %); melting point: 62°–65° C; $[\alpha]_D^{22}$ −34.1°(c=1.04 %, DMF)

Elemental analysis, for C$_{23}$H$_{33}$O$_8$N$_7$1/2H$_2$O Calcd. C, 50.73; H, 6.29; N, 18.01 Found C, 50.98; H, 6.36; N, 17.72

(b) Preparation of Z-β-Ala-Arg(NO$_2$)-Pro-OH

In 30 ml. of acetone was dissolved 2.82 g. of Z-β-Ala-Arg(NO$_2$)-Pro-OMe and, under cooling with ice, 10.7 ml. of 1N aqueous sodium hydroxide was added. The mixture was stirred at room temperature for 2 hours. After the mixture was neutralized with 11 ml. of 1N hydrochloric acid, the acetone was distilled off under reduced pressure. To the oily residue was added 30 ml. of cold water and the water was removed by decantation. The residue was washed once with cold water and dried. It was then chromatographed on a column of silica gel (90 g.) with a developer solvent, ethyl acetate-pyridine-acetic acid-water(60:20:6:11). The fractions rich in the contemplated compound were pooled and concentrated to dryness under reduced pressure. The residue was washed with ether and collected by filtration. Yield 2.62 g., melting point: 65-67° C; $[\alpha]_D^{22}$ −27.5°(c=1.07 %, DMF).

Elemental analysis, for C$_{22}$H$_{31}$O$_8$N$_7$ Calcd. C, 50.66; H, 5.99; N, 18.80 Found C, 50.41; H, 6.19; N, 18.58

(c) Preparation of Z-β-Ala-Arg(NO$_2$)-Pro-Phe-Phe-Tyr-NH$_2$

In 15 ml. of DMF was dissolved 1.50 g. of Z-Phe-Phe-Tyr-NH$_2$ and catalytic reduction was carried out with Pd-black as a catalyst for 4 hours. The catalyst was filtered off and, while the filtrate was cooled with ice, 1.21 g. of Z-β-Ala-Arg(NO$_2$)-Pro-OH, 0.53 g. of HONB and 0.61 g. of DCC were added. The mixture was stirred for 18 hours. The formed DC-urea was filtered off and the DMF was evaporated by distillation under reduced pressure. To the residue was added 50 ml. of water and the resulting powder was collected by filtration and dried. The powder was reprecipitated from DMF-ethyl acetate. Yield 1.99 g. (80.9%); melting point: 135-138° C; $[\alpha]_D^{22}$ −33.1°(c=0.9%, DMF)

Elemental analysis, for C$_{49}$H$_{59}$O$_{11}$N$_{11}$.H$_2$O Calcd. C, 59.08; H, 6.17; N, 15.47 Found C, 58.93; H, 6.18; N, 15.02

(d) Preparation of β-Ala-Arg-Pro-Phe-Phe-Tyr-NH$_2$

In 40 ml. of glacial acetic acid was dissolved 1.50 g. of Z-β-Ala-Arg(NO$_2$)-Pro-Phe-Phe-Tyr-NH$_2$ and catalytic reduction was carried out with Pd-black as a catalyst for 8 hours. The catalyst was removed by filtration and the solvent was distilled off under reduced pressure.

The residue was dissolved in 50 ml. of water and the small amounts of insolubles were filtered off. The filtrate was lyophilized. The product was further dissolved in 20 ml. of water and run through a column (3.0 × 28 cm) of carboxymethyl-cellulose, which was eluted by the gradient method with 0.005M and 0.2M aqueous ammonium acetate(1.5 l. each). The fractions from 1490 ml. to 1840 ml. were pooled and lyophilized. Yield 980 mg. (65.7 %), $[\alpha]_D^{22}$ −59.1°(C=0.52%, water)

Elemental analysis, for C$_{41}$H$_{54}$O$_7$N$_{10}$.2C$_2$H$_4$O$_2$.4H$_2$O Calcd. C, 54.53; H, 7.12; N, 14.13 Found C, 54.34; H, 6.98; N, 13.98 Amino acid analysis: Arg, 1.00; Pro, 1.11; Tyr, 1.00; Phe, 2.11; β-Ala, 0.94 (peptide content 75.7%).

In the same manner as c) and d) above, the same desired compound can be produced according to the following reaction formulas.

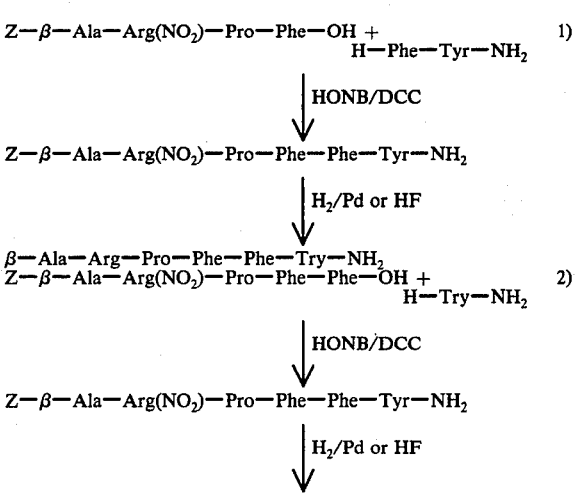

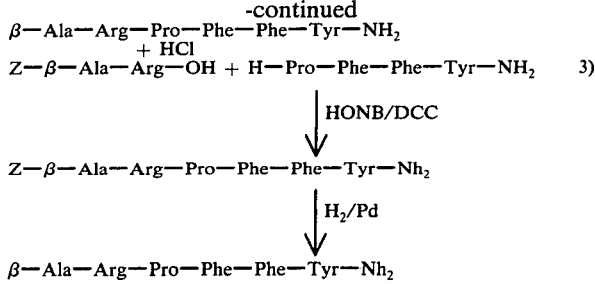

-continued

β—Ala—Arg—Pro—Phe—Phe—Tyr—NH₂
+ HCl

Z—β—Ala—Arg—OH + H—Pro—Phe—Phe—Tyr—NH₂    3)

↓ HONB/DCC

Z—β—Ala—Arg—Pro—Phe—Phe—Tyr—Nh₂

↓ H₂/Pd

β—Ala—Arg—Pro—Phe—Phe—Tyr—Nh₂

EXAMPLE 8

Production of β-Ala-Arg-Pro-Phe-Phe-NH₂

In the procedure of Example 7-c), Z-Phe-Phe-Tyr-NH₂ was replaced with Z-Phe-Phe-NH₂ and the same procedures as those set forth in Example 7-c) to d) were followed to obtain 1.24 g. of the above-indicated compound as a white fluffy product. $[\alpha]_D^{22} -48.6°(c=0.42\%,$ water)

Amino acid analysis: Arg, 1.08; Pro, 1.00; Phe, 1.98; β-Ala, 0.97 (peptide content 82.6%)

EXAMPLE 9

Production of β-Ala-Arg-β-Ala-Phe-Phe-Tyr-NH₂

(a) Preparation of Z-β-Ala-Phe-Phe-Tyr-NH₂

In 40 ml. of DMF was dissolved 2.00 g. of Z-Phe-Phe-Tyr-NH₂ and catalytic reduction was carried out with Pd-black as a catalyst for 5 hours. The catalyst was filtered off and 1.39 g. of Z-β-Ala-ONB was added to the filtrate. The mixture was stirred for 9 hours and the DMF was distilled off under reduced pressure. To the residue was added 50 ml. of water and the resulting powder was collected by filtration and dried. The product was reprecipitated from DMF-ethyl acetate. Yield 2.02 g. (88.0%); melting point:232° C, $[\alpha]_D^{22}-23.4°(c=0.94\%,$ DMF)

Elemental analysis, for $C_{38}H_{41}O_7N_5.H_2O$ Calcd. C, 65.41; H, 6.21; N, 10.04 Found C, 65.18; H, 6.20; N, 10.32

(b) Preparation of Z-Arg(NO₂)-β-Ala-Phe-Phe-Tyr-NH₂

In 30 ml. of DMF was dissolved in 1.0 g. of Z-β-Ala-Phe-Phe-Tyr-NH₂, and using Pd-black as a catalyst, catalytic reduction was carried out for 6 hours. The catalyst was filtered off. To the filtrate was added a solution of Z-Arg(NO₂)-ODNP in tetrahydrofuran (the dinitrophenyl ester prepared from 0.52 g. of Z-Arg(NO₂)-OH and 0.30 g. of 2,4-dinitrophenol in 10 ml. of tetrahydrofuran by the DCC process). The mixture was stirred for 13 hours and the solvent was distilled off. To the residue was added 50 ml. of water and the resulting powder was collected by filtration and dried. Yield 1.01 g.(74.9 %); melting point: 192°-194°; $[\alpha]_D^{22}-11.1°(c=1.02\%,$ DMF)

Elemental analysis, for $C_{44}H_{52}O_{10}N_{10}.2H_2O$ Calcd. C, 57.63; H, 6.16; N, 15.28 Found C, 57.63; H, 5.93; N, 15.61

(c) Preparation of Z-β-Ala-Arg(NO₂)-β-Ala-Phe-Phe-Tyr-NH₂

To 700 mg. of Z-Arg(NO₂)-β-Ala-Phe-Phe-Tyr-NH₂ was added 0.2 ml. of anisole, followed by the addition of 7 ml. of 25% HBr-acetic acid. The mixture was shaken at room temperature for 40 minutes. To the reaction mixture was added 100 ml. of ethyl ether and the resulting precipitate was collected by filtration and washed with ethyl ether. After drying well, the precipitate was dissolved in 10 ml. of DMF and, under cooling with ice, the solution was neutralized with triethylamine. Following the addition of 336 mg. of Z-β-Ala-ONB, the solution was stirred for 18 hours. The DMF was distilled off under reduced pressure and 50 ml. of water was added to the residue. The resulting precipitate was collected by filtration, dried and reprecipitated from DMF and ethyl acetate. Yield 560 mg. (73%); melting point: 200°-202° C (decomp.); $[\alpha]_D^{22}-7.3°(c=0.91\%,$ DMF)

Elemental analysis, for $C_{47}H_{57}O_{11}N_{11}.H_2O$ Calcd. C, 58.19; H, 6.13; N, 15.89 Found C, 58.06; H, 6.41; N, 15.57

(d) Preparation of β-Ala-Arg-β-Ala-Phe-Phe-Tyr-NH₂

In 30 ml. of glacial acetic acid was dissolved 400 mg. of Z-β-Ala-Arg(NO₂)-β-Ala-Phe-Phe-Tyr-NH₂ and catalytic reduction was carried out with Pd-black as a catalyst for 8 hours. The catalyst was removed by filtration and the solvent was distilled off under reduced pressure. The residue was dissolved in 5 ml. of water and the solution was run down a column (2.6 × 22 cm) of carboxymethyl-cellulose. Gradient elution was carried out using 0.005M and 0.2M aqueous solutions of ammonium acetate (700 ml. each). The fractions from 720 ml. to 870 ml. were pooled and lyophilized to obtain 270 mg.(69.1%) of a white fluffy product. $[\alpha]_D^{22}-17.2°(c=0.53\%,$ water)

Elemental analysis, for $C_{39}H_{52}O_7N_{10}.2C_2H_4O_2.3H_2O$ Calcd. C, 54.53; H, 7.03; N, 14.79 Found C, 54.52; H, 6.96; N, 15.00

Amino acid analysis: Arg, 1.00; Tyr, 1.00; Phe, 2.03; β-Ala, 2.14(peptide content 79.0 %)

EXAMPLE 10

Production of Ala-Arg-β-Ala-Phe-Phe-Tyr-NH₂

In the process of Example 9-c), Z-β-Ala-ONB was replaced with 340 mg. of Z-Ala-ONB and the same procedures as Example 9-c) to d) were followed to obtain 297 mg. of the above-indicated compound as a white fluffy product. $[\alpha]_D^{24}-18.9°(c=0.62\%,$ water) Amino acid analysis: Arg, 1.02; Ala, 1.04; Tyr, 0.97; Phe, 2.00; β-Ala, 0.97(peptide content 81.0 %)

EXAMPLE 11

Production of β-Ala-Arg-Sar-Phe-Phe-Tyr-NH₂

(a) Preparation of Z-Sar-Phe-Phe-Tyr-NH₂

In 30 ml. of DMF was dissolved 2.02 g. of Z-Phe-Phe-Tyr-NH₂ and catalytic reduction was carried out with Pd-black as a catalyst for 5 hours. The catalyst was filtered off and the filtrate was cooled. On the other hand, 810 mg. of Z-Sar-OH was dissolved in 10 ml. of tetrahydrofuran, followed by the addition of 0.71 g. of HONB. The mixture was cooled to 0° C and 0.82 g. of DCC was added. The mixture was stirred for 3 hours. The formed DC-urea was filtered off and the filtrate was added to the above DMF solution. The mixture was stirred for 20 hours. The solvent was distilled off under reduced pressure and 50 ml. of water was added to the residue. The resulting powder was collected by filtration and reprecipitated from DMF-ethyl acetate. Yield 1.90 g (83.8 %); melting point: 246°-248° C(decomp.); $[\alpha]_D^{23}-9.7°(c=1.07\%,$ DMF)

Elemental analysis, for $C_{38}H_{41}O_7N_5.\tfrac{1}{2}H_2O$ Calcd. C, 66.26; H, 6.15; N, 10.17 Found C, 66.32; H, 6.39; N, 10.52

(b) Preparation of Z-Arg(NO$_2$)-Sar-Phe-Phe-Tyr-NH$_2$

In 10 ml. of DMF was dissolved 1.0 g. of Z-Sar-Phe-Phe-Tyr-NH$_2$ and catalytic reduction was carried out with Pd-black as a catalyst for 7 hours. The catalyst was filtered off and the filtrate was cooled. On the other hand, 0.52 g. of Z-Arg(NO$_2$)-OH was dissolved in 10 ml. of tetrahydrofuran and, under cooling with ice, 0.3 g. of 2,4-dinitrophenol and 0.33 g. of DCC were added. The mixture was stirred for 3 hours. The formed DC-urea was filtered off and the filtrate was added to the above DMF solution. The mixture was stirred for 20 hours and the solvent was distilled off under reduced pressure. To the residue was added 50 ml. of water and the resulting powder was collected by filtration. After drying, the powder was reprecipitated from DMF-ethyl acetate-ethyl ether. Yield 1.04 g. (77.2%); melting point: 96°-98°; $[\alpha]_D^{23}$ −7.3°(c=1.06%, DMF).

Elemental analysis, for C$_{44}$H$_{52}$O$_{10}$N$_{10}$.2H$_2$O Calcd. C, 57.63; H, 6.16; N, 15.28 Found C, 57.60; H, 6.10; N, 15.01

(c) Preparation of Z-β-Ala-Arg(NO$_2$)-Sar-Phe-Phe-Tyr-NH$_2$

In 7 ml. of 25 % HBr-acetic acid were dissolved 700 mg. of Z-Arg(NO$_2$)-Sar-Phe-Phe-Tyr-NH$_2$ and 0.2 ml. of anisole and the solution was shaken at room temperature for 40 minutes. To this reaction mixture was added 100 ml. of ethyl ether and the resulting precipitate was collected by filtration, washed with ether and dried over sodium hydroxide pellets for 2 hours.

The dried precipitate was dissolved in 10 ml. of DMF and, under cooling with ice, the solution was neutralized with triethylamine. Following the addition of 336 mg. of Z-β-Ala-ONB, the solution was stirred for 20 hours. The DMF was distilled off under reduced pressure and 50 ml. of water was added. The resulting powder was collected by filtration, dried and reprecipitated from DMF-ethyl acetate. Yield 590 mg. (76.5%); melting point: 135°-138° C; $[\alpha]_D^{23}$ −15.5°(c=0.99%, DMF)

Elemental analysis, for C$_{47}$H$_{57}$O$_{11}$N$_{11}$.H$_2$O Calcd. C, 58.19; H, 6.13; N, 15.89 Found C, 58.18; H, 6.40; N, 15.60

(d) Preparation of β-Ala-Arg-Sar-Phe-Phe-Tyr-NH$_2$

In 30 ml. of acetic acid was dissolved 450 mg. of Z-β-Ala-Arg(NO$_2$)-Sar-Phe-Phe-Tyr-NH$_2$ and catalytic reduction was carried out with Pd-black as a catalyst for 8 hours. The catalyst was filtered off and the filtrate was concentrated to dryness under reduced pressure. The residue was dissolved in 5 ml. of water and chromatographed on a column (2.6 × 22 cm) of carboxymethyl-cellulose. Gradient elution was carried out with 0.005M and 0.2M aqueous solutions of ammonium acetate (700 ml. each), whereupon the desired compound emerged in fractions from 770 ml. to 880 ml. These fractions were pooled and lyophilized to obtain 309 mg. (70.4%) of a white fluffy product. $[\alpha]_D^{22}$ −21.5°(c=0.46%, water)

Elemental analysis, for C$_{39}$H$_{52}$O$_7$N$_{10}$.2C$_2$H$_4$O$_2$.3H$_2$O Calcd. C, 54.53; H, 7.03; N, 14.79 Found C, 54.99; H, 6.76; N, 14.58

Amino acid analysis: Arg, 1.00; Tyr, 0.88; Phe, 2.02; β-Ala, 0.98; Sar(not determined)(peptide content 78.7 %)

EXAMPLE 12

Production of Leu-Arg-Pro-Phe-Phe-Tyr-NH$_2$ (a) Preparation of Z-Leu-Arg(NO$_2$)-Pro-Phe-Phe-Tyr-NH$_2$ In 20 ml. of DMF was dissolved 700 mg. of Z-Phe-Phe-Tyr-NH$_2$ and catalytic reduction was carried out with Pd-black as a catalyst for 6 hours. The catalyst was filtered off and the filtrate was cooled. To this filtrate was added 648 mg. of Z-Leu-Arg(NO$_2$)-Pro-OH, followed by addition of 247 mg. of HONB and 285 mg. of DCC. The mixture was stirred for 20 hours. The formed DC-urea was filtered off and the DMF was distilled off under reduced pressure. To the residue was added 50 ml. of water and the resulting powder was collected by filtration, dried and reprecipitated from DMF-ethyl acetate-ether. Yield 1.05 g. (86.5%); melting point: 110–111° C; $[\alpha]_D^{22}$ −38.1°(c=1.0%, DMF)

Elemental analysis, for C$_{52}$H$_{65}$O$_{11}$N$_{11}$.2H$_2$O Calcd. C, 59.13; H, 6.59; N, 14.59 Found C, 59.24; H, 6.50; N, 14.62

(b) Production of Leu-Arg-Pro-Phe-Phe-Tyr-NH$_2$

In 20 ml. of acetic acid was dissolved 500 mg. of Z-Leu-Arg(NO$_2$)-Pro-Phe-Phe-Tyr-NH$_2$ and catalytic reduction was carried out with Pd-black as a catalyst for 10 hours.

The catalyst was filtered off and the filtrate was concentrated to dryness under reduced pressure. The residue was dissolved in 5 ml. of water and chromatographed on a column (2.6 × 20 cm) of carboxymethyl-cellulose. Gradient elution was carried out with 0.005M and 0.2M aqueous solutions of ammonium acetate (700 ml. each), whereupon the desired compound emerged in fractions from 700 ml. to 790 ml. The fractions were pooled and lyophilized to obtain 300 mg. (63.6 %) of a white fluffy product. $[\alpha]_D^{22}$ −58.3°(c=0.59%, water)

Elemental analysis, for C$_{44}$H$_{60}$O$_7$N$_{10}$.2C$_2$H$_4$O$_2$.2H$_2$O Calcd. C, 57.81; H, 7.28; N, 14.05 Found C, 57.72; H, 7.24; N, 14.25 Amino acid analysis: Arg, 1.07; Gly, 1.03; Tyr, 0.87; Phe, 2.07; Phe, 1.00 (peptide content 83.9%)

EXAMPLE 13

Production of β-Ala-Arg-Phe-Phe-Phe-Tyr-NH$_2$ (a) Preparation of Z-β-Ala-Arg(NO$_2$)-Phe-Phe-Phe-Tyr(Bzl)resin In the reaction vessel of a solid-phase peptide synthesizer (Simadzu APS-800, Simadzu Seisakusho, Japan) was put 4.33 g. of BOC-Tyr(Bzl)-resin (Tyr content 2.18 mM) and, after swelling with dichloromethane, BOC-Phe-OH, BOC-Phe-OH, BOC-Phe-OH, BOC-Arg(NO$_2$) and Z-β-Ala-OH were introduced in the indicated order by the DCC method in accordance with the method of Merrifield (See J.A.C.S. 86, 304(1964)). After all the reactions had been completed, the resin was washed with dichloromethane, DMF, ethanol, glacial acetic acid and methanol, followed by drying. The above procedure yielded 6.55 g. of peptide-resin.

(b) Preparation of Z-β-Ala-Arg(NO$_2$)-Phe-Phe-Phe-Tyr(Bzl)-NH$_2$

In 50 ml. of 17% ammonia-methanol was suspended 6.04 g. of the resin obtained in a) above and the suspension was stirred at room temperature for 48 hours. The resin was filtered off and the filtrate was concentrated to dryness under reduced pressure. To the residue was added ether and the resulting powder was collected by filtration and dried. Yield 2.43 g.

(c) Production of β-Ala-Arg-Phe-Phe-Phe-Tyr-NH$_2$

In 30 ml. of glacial acetic acid was dissolved 500 mg. of the crude protected peptide-amine obtained in b), and catalytic reduction was carried out with Pd-black as a catalyst for 10 hours. The catalyst was filtered off and the filtrate was concentrated to dryness under reduced pressure. The residue was dissolved in 5 ml. of water and the solution was run down a column (2.6 × 24.5 cm) of carboxymethyl-cellulose. Gradient elution was carried out with 0.005M and 0.2M aqueous solutions of ammonium acetate (800 ml. each). The fractions from 1180 ml. to 1545 ml. were pooled and lyophilized. Yield 237 mg. (64 %); $[\alpha]_D^{24} - 33.19°(c=0.46\%$, water)

Elemental analysis, for $C_{45}H_{54}O_7N_9.2C_2H_4O_2.3H_2O$ Calcd. C, 58.44; H, 6.81; N, 12.52 Found C, 58.44; H, 6.24; N, 12.86

Amino acid analysis: Arg, 1.00; Tyr, 0.81; Phe, 3.20; β-Ala, 0.9(peptide content 84.8 %)

EXAMPLE 14

Production of β-Ala-Arg-Leu-Phe-Phe-Tyr-Gly-NH₂

(a) Preparation of Z-β-Ala-Arg(Tos)-Leu-Phe-Phe-Tyr(Bzl)-Gly-resin

In the reaction vessel of a solid-phase peptide synthesizer (Simadzu APS-800) was put 4.0 g. of BOC-Gly-resin (containing 1.7 mM equivalent of Gly), which was then swollen with dichloromethane for 20 hours. To the reaction vessel were introduced BOC-Phe-OH, BOC-Phe-OH, BOC-Leu-OH, Aoc-Arg(Tos)-OH, and Z-β-Ala-OH in the order mentioned, with DCC as a condensing agent and trifluoroacetic acid-dichloromethane (1:1) as a agent for removal of BOC. After all the reactions were completed, the resin was washed with dichloromethane, DMF, methanol, glacial acetic acid and methanol, followed by drying. Yield 5.09 g.

(b) Preparation of Z-β-Ala-Arg(Tos)-Leu-Phe-Phe-Tyr(Bzl)-Gly-NH₂

In 50 ml. of 17% ammonia-methanol was suspended 4.4 g. of the resin prepared in a) above and, after the vessel was sealed tight, the suspension was stirred at room temperature for 48 hours.

The resin was filtered off and washed with DMF. The filtrates were combined and concentrated to dryness under reduced pressure. To the residual oil was added ether and the resulting powder was collected by filtration. Yield 950 mg.

(c) Preparation of β-Ala-Arg-Leu-Phe-Phe-Tyr-Gly-NH₂

To 500 mg. of the crude protected peptide-amide prepared in b) was added 0.5 ml. of anisole and the mixture was then added to 10 ml. of hydrogen fluoride. The mixture was stirred at 0° C for 60 minutes and the hydrogen fluoride was distilled off under reduced pressure. The residue was dissolved in 50 ml. of water. The solution was washed twice with 20 ml. of ether, passed down a column (1 × 10 cm) of Amberlite IRA-410(acetate-form), and lyophilized. The product was dissolved in 20 ml. of water and the solution was run down a column (2.6 × 25 cm) of carboxymethylcellulose. Gradient elution was carried out using 0.005M and 0.2M aqueous solutions of ammonium acetate (800 ml. each). The fractions from 1200 ml. to 1530 ml. were pooled and lyophilized. The procedure yielded 167 mg. of a white fluffy product. $[\alpha]_D^{23} - 28.93°(c=0.6\%$, water)

Elemental analysis, for $C_{44}H_{61}O_8N_{11}.2C_2H_4O_2.3.5H_2O$ Calcd. C, 54.64; H, 7.26; N, 14.60 Found C, 54.64; H, 7.58; N, 14.37 Amino acid analysis: Arg, 1.06; Gly, 1.00; Leu, 1.11; Tyr, 0.87; Phe, 2.09; β-Ala, 1.14(peptide content 82.0%)

EXAMPLE 15

Production of β-Ala-Arg-Ser-Phe-Phe-Tyr-Gly-NH₂

(a) Preparation of Z-β-Ala-Arg(Tos)-Ser(Bzl)-Phe-Phe-Tyr(Bzl)-Gly-resin

In the reaction vessel of a solid-phase peptide synthesizer (Model APS-800 of Simadzu Siesakusho, Japan) was put 4.02 g. of BOC-Gly-resin (containing 2.17 m mol of Gly) and BOC-Tyr(Bzl)-OH, BOC-Phe-OH, BOC-Phe-OH, BOC-Ser (Bzl)-OH, Aoc-Arg(Tos)-OH and Z-β-Ala-OH were introduced in the order mentioned according to the method of Merrifield. After all the reactions had been completed, the resin was washed with dichloromethane, methanol, DMF, glacial acetic acid and methanol, followed by drying. Yield 6.4 g.

(b) Preparation of Z-β-Ala-Arg(Tos)-Ser(Bzl)-Phe-Phe-Tyr(Bzl)-Gly-NH₂

In 50 ml. of 17 % ammonia-methanol was suspended 5.9 g. of the resin prepared in a) and the suspension was stirred at room temperature for 48 hours. The resin was filtered off and washed with DMF. The washings were combined with the filtrate and the combined solution was concentrated to dryness under reduced pressure. To the residue was added ether and the resulting powder was collected by filtration. Yield 2.02 g.

(c) Preparation of β-Ala-Arg-Ser-Phe-Phe-Tyr-Gly-NH₂

In 10 ml. of anhydrous hydrogen fluoride were dissolved 1.0 g. of the crude protected peptide-amide prepared in b) and 1 ml. of anisole and the solution was stired at 0° C for 60 minutes. The hydrogen fluoride was distilled off under reduced pressure and the residue was dissolved in 20 ml. of water. The solution was washed twice with 10 ml. of ether, passed down a column (1.0 × 15 cm) of Amberlite IRA-410 and lyophilized. The product was dissolved in 10 ml. of water and the solution was run onto a column (2.5 × 25 cm) of carboxymethyl-cellulose. Gradient elution was carried out with 0.005M and 0.2M aqueous solutions of ammonium acetate (800 ml. each). The fractions from 800 ml. to 950 ml. were pooled and lyophilized. The product was further passed through a column (2 × 10 cm) of Amberlite XAD-2 (Polystyrene resin of Rohm & Haas Co. Ltd., U.S.A.) (water) and lyophilized. The procedure yielded 55 mg. of the above-indicated compound as a white fluffy product. $[\alpha]_D^{24} - 30.11°(c=0.47\%$, water)

Amino acid analysis: Arg, 1.04; Ser, 0.96; Gly, 1.00; Tyr, 0.88; Phe, 2.10; β-Ala, 0.98(peptide content 83.0 %).

EXAMPLE 16

Production of β-Ala-Arg-Pro-Phe-Phe-Tyr-Thr-Pro-Lys-Ala-OH

In 30 ml. of methanol was dissolved 1.16 g. of Z-Phe-Phe-Tyr-Thr-Pro-Lys(BOC)-Ala-O'Bu and catalytic reduction was carried out with Pd-black as a catalyst for 4 hours. The catalyst was filtered off and the filtrate was concentrated to dryness under reduced pressure. The residue was dissolved in 15 ml. of DMF. To this solution were added 492 mg. of Z-β-Ala-Arg(NO₂)-Pro-OH and 200 mg. of HONB, and under cooling, 250 mg. of DCC was added. The mixture was stirred for 18 hours.

The insolubles were filtered off and the DMF was distilled off under reduced pressure. To the residue was added ethyl acetate and the resulting powder was dried and dissolved in 10 ml. of trifluoroacetic acid. The solution was allowed to stand for 40 minutes. The trifluoroacetic acid was distilled off under reduced pressure and the residue was dissolved in 30 ml. of glacial acetic acid. Catalytic reduction was carried out with Pd-black as a catalyst for 16 hours.

The catalyst was filtered off and the filtrate was concentrated to dryness under reduced pressure and dissolved in 10 ml. of water. After an ion exchange with Amberlite IRA-410, the small amounts of insolubles were filtered off and the filtrate was run down a column (2.2 × 30 cm) of carboxymethyl-cellulose. Gradient elution was carried out with 0.005M and 0.2M aqueous solutions of ammonium acetate (800 ml. each). The fractions from 820 ml. to 1180 ml. were pooled and lyophilized. The procedure yielded 670 mg. of a white fluffy product.

Amino acid analysis: Lys, 1.02; Arg, 0.98; Thr, 0.96; Pro, 2.04; Ala, 1.00; Tyr, 0.87; Phe, 2.02; β-Ala, 1.05(peptide content 74%).

EXAMPLE 17

Production of β-Ala-Arg-Gly-Phe-Phe-Tyr-Leu-OH (a) Preparation of Z-Phe-Phe-Tyr-OEt In 30 ml. of ethanol was dissolved 3.43 g. of Z-Phe-Tyr-OEt and catalytic reduction was carried out with Pd-black as a catalyst for 2 hours. The catalyst was filtered off and the solvent was evaporated by distillation under reduced pressure. The residue was dissolved in 15 ml. of DMF, and 2.77 g. of Z-Phe-OSu was added. The mixture was stirred for 10 hours. To this reaction mixture was added 80 ml. of water and the resulting crystals were collected by filtration and recrystallized from ethanol-ethyl acetate-ethyl ether. The procedure yielded 3.72 g. (83.4%) of needles melting at 185–186° C; $[\alpha]_D^{24} - 18.1°(c = 1.09\%, DMF)$.

Elemental analysis, for $C_{37}H_{39}O_7N_3$ Calcd. C, 69.68; H, 6.16; N, 6.59 Found C, 69.64; H, 6.14; N, 6.54

(b) Preparation of Z-β-Ala-Arg(NO$_2$)-Gly-Phe-Phe-Tyr-OEt

In 50 ml. of ethanol was suspended 2.0 g. of Z-Phe-Phe-Tyr-OEt and catalytic reduction was carried out with Pd-black as a catalyst for 1.5 hours. The catalyst was removed by filtration and the solvent was distilled off under reduced pressure. The residue was dissolved in 20 ml. of DMF. Under cooling with ice, 1.56 g. of Z-β-Ala-Arg(NO$_2$)-Gly-OH, 0.7 g. of HONB and 0.8 g. of DCC were added to the above solution and the mixture was stirred for 12 hours.

The formed urea derivative was filtered off and the DMF was distilled off under reduced pressure. To the residue was added 60 ml. of water and the resulting powder was collected by filtration, dried and reprecipitated from DMF-ethyl acetate. Yield 2.58 g. (82%); melting point: 83–85° C; $[\alpha]_D^{25} - 10.0°(c = 1.1\%, DMF)$.

Elemental analysis, for $C_{48}H_{58}O_{12}N_{10}.2H_2O$ Calcd. C, 57.43; H, 6.23; N, 13.97 Found C, 57.41; H, 6.05; N, 14.49

(c) Preparation of Z-β-Ala-Arg(NO$_2$)-Gly-Phe-Phe-Tyr-OH

In 30 ml. of acetone was suspended 2.00 g. of Z-β-Ala-Arg(NO$_2$)-Gly-Phe-Phe-Tyr-OEt and, under cooling with ice, 6.3 ml. of 1N aqueous sodium hydroxide was added. Then, at room temperature, the mixture was stirred for 1 hour. Following the addition of 3 ml. of 1N hydrochloric acid, the acetone was distilled off under reduced pressure. The small amounts of insolubles were filtered off and 3.8 ml. of 1N hydrochloric acid was added. The resulting precipitate was collected by filtration, washed well with cold water and dried. Yield 1.96 g. (98%); melting point: 70°–73° C; $[\alpha]_D^{26} - 8.7°(c = 0.97\%, DMF)$ Elemental analysis, for $C_{46}H_{54}O_{12}N_{10}.H_2O$ Calcd. C, 57.77; H, 5.90; N, 14.64 Found C, 58.13; H, 5.89; N, 14.51

(d) Preparation of Z-β-Ala-Arg(NO$_2$)-Gly-Phe-Phe-Tyr-Leu-OBzl

In 5 ml. of DMF was dissolved 275 mg. of H-Leu-OBzl-p-toluenesulfonate and the solution was neutralized with 0.9 ml. of 10% N-ethylmorpholine-DMF. Under cooling at -10° C, 670 mg. of Z-β-Ala-Arg(NO$_2$)-Gly-Phe-Phe-Tyr-OH, 251 mg. of HONB and 289 mg. of DCC were added. The mixture was stirred for 12 hours and the formed DC-urea was filtered off. The DMF was distilled off under reduced pressure and 30 ml. of water was added to the residue. The resulting precipitate was collected by filtration, washed with hot methanol and dried. Yield 703 mg. (87.9%) melting point: 178–181° C; $[\alpha]_D^{23} - 15.0°(c = 1.02\%, DMF)$ Elemental analysis, for $C_{59}H_{72}O_{13}N_{11}$ Calcd. C, 61.98; H, 6.35; N, 13.49 Found C, 61.88; H, 6.78; N, 13.15

(e) Production of β-Ala-Arg-Gly-Phe-Phe-Tyr-Leu-OH

In 30 ml. of acetic acid was dissolved 500 mg. of Z-β-Ala-Arg(NO$_2$)-Gly-Phe-Phe-Tyr-Leu-OBzl, and catalytic reduction was carried out with Pd-black as a catalyst for 8 hours. The catalyst was filtered off and the solvent was evaporated by distillation under reduced pressure. The residue was dissolved in 5 ml. of water and the solution was run onto a column (2.6 × 18 cm) of carboxymethyl-cellulose. Elution was carried out by the linear gradient method using 0.005M aqueous ammonium acetate (700 ml.) and 0.2M-aqueous ammonium acetate (700 ml.), whereupon the aboveindicated compound emerged in fractions from 370 ml. to 720 ml. These fractions were pooled and lyophilized. Yield 277 mg. (64.2 %); $[\alpha]_D^{23} - 32.5°(c = 0.51\%, water)$.

Elemental analysis, for $C_{44}H_{60}O_9N_{10}.C_2H_4O_2.3H_2O$ Calcd. C, 55.97; H, 7.15; N, 14.19 Found C, 55.80; H, 7.20; N, 14.17

Amino acid analysis: Arg, 1.00; Gly, 1.04; Leu, 1.08; Phe, 2.16; Tyr, 0.88; β-Ala, 1.04(peptide content 85.9 %)

EXAMPLE 18

Production of β-Ala-Arg-Gly-Phe-Phe-Tyr-Ala-NH$_2$

The procedures described in Example 17-d) and -e) were repeated except that H-Ala-NH$_2$.hydrochloride was used in place of H-Leu-OBzl-p-toluenesulfonate, whereby β-Ala-Arg-Gly-Phe-Phe-Tyr-Ala-NH$_2$.diacetate was obtained in a yield of 216 mg.

Amino acid analysis: Arg, 1.01; Gly, 1.00; Ala, 1.02; Phe, 2.00; Tyr, 0.89, β-Ala, 1.12(peptide content 82.4 %)

EXAMPLE 19

Production of β-Ala-Arg-Gly-Phe-Phe-Tyr-Thr-Pro-OH (a) Preparation of Z-Phe-Phe-Tyr-Thr-Pro-O$^t$Bu In 30 ml. of methanol was dissolved 1.80 g. of Z-Thr-Pro-O$^t$Bu and catalytic reduction was carried out with Pd-black as a catalyst for 5 hours. The catalyst was filtered off and the solvent was distilled off under reduced pressure. The residue was dissolved in 20 ml. of DMF and, after the solution was cooled to −10° C, 2.70 g. of Z-Phe-Phe-Tyr-OH, 1.59 g. of HONB and 1.37 g. of DCC were added. The mixture was stirred for 18 hours. The formed urea derivative was filtered off and 100 ml. of water was added. The resulting precipitate was collected by filtration, dried and dissolved in 100 ml. of ethyl acetate. The solution was washed twice with 50 ml. of water and dried over anhydrous sodium sulfate. The solvent was then distilled off and ethyl acetate was added to the residue. The resulting powder was collected by filtration and dried. Yield 2.51 g. (89.8 %); melting point: 137–139° C; $[\alpha]_D^{25}$ −44.1°(c=1.08%, DMF)

Elemental analysis, for $C_{48}H_{57}O_{10}N_5 \cdot H_2O$ Calcd. C, 65.36; H, 6.74; N, 7.94 Found C, 65.49; H, 6.82; N, 7.91

(b) Preparation of Z-β-Ala-Arg(NO₂)-Gly-Phe-Phe-Tyr-Thr-Pro-O'Bu

In 20 ml. of methanol was dissolved 1.50 g. of Z-Phe-Phe-Tyr-Thr-Pro-O'Bu and catalytic reduction was carried out with Pd-black as a catalyst in a current of hydrogen for 4 hours. The catalyst was filtered off and the solvent was evaporated by distillation under reduced pressure.

The residue was dissolved in 10 ml. of DMF and while the solution was cooled with ice, 0.87 g. of Z-β-Ala-Arg-(NO₂)-Gly-OH, 0.47 g. of HONB and 0.54 g. of DCC were added. The mixture was stirred for 16 hours. The formed DC-urea was filtered off and 50 ml. of water was added to the filtrate, whereupon a gel separated out. This precipitate was collected by filtration, dried and reprecipitated from DMF-ethyl acetate. The precipitate was collected by filtration and further reprecipitated from ethanol. Yield 1.40 g. (67.4%) melting point: 153°-156°; $[\alpha]_D^{25}$ −32.3°(c=0.97%, DMF).

Elemental analysis, for $C_{59}H_{76}O_{15}N_{12}$ Calcd. C, 58.50; H, 6.57; N, 13.88 Found C, 58.24; H, 6.54; N, 13.87

(c) Production of β-Ala-Arg-Gly-Phe-Phe-Tyr-Thr-Pro-OH

To 900 mg. of Z-β-Ala-Arg(NO₂)-Gly-Phe-Phe-Tyr-Thr-Pro-O'Bu was added 0.9 ml. of anisole, followed by the addition of 10 ml. of anhydrous hydrogen fluoride. The mixture was stirred at −4° C for 30 minutes. The hydrogen fluoride was distilled off under reduced pressure and 30 ml. of water was added to the residue.

The solution was extracted with 30 ml. of ethyl ether and the equeous layer was run through a column (1.0 × 10.0 cm) of Amberlite IRA-410(acetate-form), which was washed with water. The aqueous washings were pooled with the effluent and the combined solution was lyophilized. The product was dissolved in 10 ml. of water and the solution was passed through a column (2.2 × 21 cm) of carboxymethyl-cellulose. Gradient elution was carried out with 0.005M aqueous ammonium acetate (700 ml.) and 0.3M aqueous ammonium acetate (700 ml.), whereupon the desired compound emerged in fractions from 235 ml. to 385 ml. These fractions were pooled and lyophilized. Yield 476 mg. (57.0%) $[\alpha]_D^{25}$ −38.8°(c=0.25%, water)

Elemental analysis, for $C_{47}H_{63}O_{11}N_{11} \cdot C_2H_4O_2 \cdot 5H_2O$ Calcd. C, 53.10; H, 7.00; N, 13.91 Found C, 53.27; H, 7.04; N, 13.82

Amino acid analysis: Arg, 1.05; Thr, 1.00; Pro, 1.02; Gly, 0.95; Tyr, 0.95; Phe, 2.02; β-Ala, 0.93 (peptide content 85.5%)

EXAMPLE 20

Production of ε-Acap-Arg-Gly-Phe-Phe-Tyr-Thr-Pro-OH (a) Preparation of Z-ε-Acap-Arg(NO₂)-Gly-OEt To 2.41 g. of Z-Arg(NO₂)-Gly-OEt was added 12 ml. of 25% HBr-acetic acid and the mixture was shaken at room temperature for 40 minutes. To the solution was added ethyl ether and the resulting precipitate was collected by filtration and dried over sodium hydroxide.

On the other hand, 1.33 g. of Z-ε-Acap-OH and 0.99 g. of HONB were dissolved in 5 ml. of tetrahydrofuran and, under cooling with ice, 1.14 g. of DCC was added. The mixture was stirred for 4 hours and the formed dicyclohexylurea was filtered off. The above amine component was dissolved in 10 ml. of DMF and, after the solution was neutralized with triethylamine, the above active ester solution was added. The mixture was stirred overnight. The solvent was distilled off under reduced pressure and the residue was dissolved in 50 ml. of ethyl acetate. The solution was washed with water and, then, with a saturated aqueous solution of sodium hydrogen carbonate (50 ml. × 2), It was washed with water and dried over anhydrous sodium sulfate. The solvent was distilled off under reduced pressure and petroleum benzin was added to the residue. The resulting crystals are recrystallized from water-ethanol-ethyl acetate. Yield 2.1 g. (76%); melting point: 85-87° C; $[\alpha]_D^{24}$ −11.9°(c=1.0%, DMF).

Elemental analysis, for $C_{24}H_{37}O_8N_7$ Calcd. C, 52.26; H, 6.76; N, 17.78 Found C, 52.43; H, 6.64; N, 17.76

(b) Preparation of Z-ε-Acap-Arg(NO₂)-Gly-OH

In 10 ml. of acetone was dissolved 1.8 g. of Z-ε-Acap-Arg(NO₂)-Gly-OEt and, after cooling with ice, 2.9 ml. of 2N sodium hydroxide was added. At room temperature, the mixture was stirred for 2 hours. To the mixture was added 2.5 ml. of 1N hydrochloric acid and the acetone was distilled off. To the residue was added 10 ml. of water and, after the insolubles were filtered off, the solution was rendered acidic with 1N hydrochloric acid. The resulting crystals were collected by filtration. Yield 1.59 g. (93%); melting point: 97.5°-99° C; $[\alpha]_D^{24}$ −10.7°(c=1.0%, DMF)

Elemental analysis, for $C_{22}H_{33}O_8N_7 \cdot H_2O$ Calcd. C, 48.79; H, 6.52; N, 18.10 Found C, 48.50; H, 6.28; N, 18.23

(c) Production of ε-Acap-Arg-Gly-Phe-Phe-Tyr-Thr-Pro-OH

In the process of Example 19-b), Z-β-Ala-Arg(NO₂)-Gly-OH was replaced with Z-ε-Acap-Arg(NO₂)-Gly-OH and the same procedures as set forth in Example 19-b) and c) were repeated to obtain 428 mg. of the above-indicated compound. $[\alpha]_D^{24}$ −37.9°(c=0.25%, water)

Amino acid analysis: Arg, 1.02; Thr, 1.02; Pro, 1.00; Gly, 1.01; Phe, 2.04; Tyr, 0.92; ε-Acap (not determined) (peptide content 84.9%)

EXAMPLE 21

Production of Lys-Arg-Gly-Phe-Phe-Tyr-Thr-Pro-OH (a) Preparation of di-Z-Lys-Arg(NO₂)-Gly-OEt Using 2.07 g. of di-Z-Lys-OH, the above-indicated compound was obtained as a gel in the same manner as Example 20-a). The gel was reprecipitated from water-ethanol-ethyl acetate. Yield 2.57 g. (73%); melting point: 161°-162° C; $[\alpha]_D^{24}$ −11.9°(c=1.0%, DMF)

Elemental analysis, for $C_{32}H_{44}O_{10}N_8$ Calcd. C, 54.85; H, 6.33; N, 15.99 Found C, 54.45; H, 6.05; N, 15.99

(b) Preparation of di-Z-Lys-Arg($NO_2$)-Gly-OH

In 10 ml. of acetone was dissolved 2.0 g. of di-Z-Lys-Arg($NO_2$)-Gly-OEt and, under cooling with ice, 2.1 ml. of 2N sodium hydroxide was added. Then, at room temperature, the mixture was stirred for 2 hours. Following the addition of 1.4 ml. of 1N hydrochloric acid, the acetone was distilled off under reduced pressure and 10 ml. of water was added to the residue.

The insolubles were filtered off and the filtrate was rendered acidic with 1N hydrochloric acid. The resulting gels were collected by filtration. Yield 1.78 g. (93%); melting point: 131°–132.5° C; $[\alpha]_D^{24}$ −10.5°(c=1.0%,DMF)

Elemental analysis, for $C_{30}H_{40}O_{10}N_8 \cdot 3/2H_2O$ Calcd. C, 51.49; H, 6.20; N, 16.02 Found C, 51.43; H, 5.92; N, 16.23

(c) Preparation of Lys-Arg-Gly-Phe-Phe-Tyr-Thr-Pro-OH

The procedure of Example 19-b) was repeated except that di-Z-Lys-Arg($NO_2$)-Gly-OH was used in place of Z-β-Ala-Arg($NO_2$)-Gly-OH to produce 452 mg. of the above-indicated compound. $[\alpha]_D^{28}$ −34.8°(c=0.4%, water)

Amino acid analysis: Lys, 1.08; Arg, 1.01; Thr, 0.92; Pro, 1.00; Gly, 1.00; Phe, 2.08; Tyr, 0.89(peptide content 85.2%)

EXAMPLE 22

Production of β-Ala-Arg-Gly-Phe-Phe-Tyr-Thr-Pro-Lys-Ala-OH (a) Preparation of Z-Lys(BOC)-Ala-O$^t$Bu In 300 ml. of methanol was dissolved 14. g. of Z-Ala-O$^t$Bu, and catalytic reduction was carried out with Pd-black as a catalyst for 2 hours. The catalyst was filtered off and the methanol was distilled off.

The residue was dissolved in 50 ml. of tetrahydrofuran. On the other hand, 28.1 g. of Z-Lys(BOC)-OH dicyclohexylamine salt was suspended in 300 ml. of ethyl acetate and washed three times with 200 ml. of 0.5N sulfuric acid. After washing with water, it was dried over anhydrous sodium sulfate.

The ethyl acetate was partially distilled off to a volume of about 150 ml. The residue was added to the above tetrahydrofuran solution, followed by the addition of 10 g. of HONB. Under cooling with ice, 11.3 g. of DCC was added and the mixture was stirred for 16 hours. The formed DC-urea was filtered off and the filtrate was concentrated to dryness. The residue was dissolved in 500 ml. of ethyl acetate and washed with 0.5N sulfuric acid and 4% aqueous sodium hydrogen carbonate. After washing well with water, the ethyl acetate layer was dried over anhydrous sodium sulfate. The solvent was evaporated to dryness under reduced pressure and petroleum benzin was added, whereupon crystals separated. These crystals were collected by filtration and recrystallized from ethyl acetate-petroleum benzin. Yield 21.9 g. (87%); melting point: 55°-57° C; $[\alpha]_D^{23}$ −30.17°(c=1.16%, methanol).

Elemental analysis, for $C_{26}H_{41}O_7N_3$ Calcd. C, 61.52; H, 8.14; N, 8.28 Found C, 61.61; H, 8.10; N, 8.18

(b) Preparation of Z-Pro-Lys(BOC)-Ala-O$^t$Bu

In 40 ml. of methanol was dissolved 2.5 g. of Z-Lys(BOC)-Ala-O$^t$Bu and catalytic reduction was carried out with Pd-black as a catalyst for 2 hours. The catalyst was filtered off and the filtrate was concentrated to dryness under reduced pressure. The residue was dissolved in 20 ml. of ethyl acetate. To this solution was added 2.45 g. of Z-Pro-ONB and the mixture was stirred at room temperature for 18 hours. To this solution was added 200 ml. of ethyl acetate and the mixture was washed with 0.5N sulfuric acid and 4% aqueous sodium hydrogen carbonate. It was then washed three times with water, dried over anhydrous sodium sulfate and concentrated to dryness under reduced pressure. To the residue was added petroleum benzin and the resulting crystals were collected by filtration and recrystallized from ethyl acetate-petroleum benzin. Yield 2.53 g. (85%); melting point: 127°–129° C; $[\alpha]_D^{23}$ −64.52°(c=1.04%, methanol)

Elemental analysis, for $C_{31}H_{48}O_8N_4$ Calcd. C, 61.57; H, 8.00; N, 9.27 Found C, 61.81; H, 8.31; N, 9.37

(c) Preparation of Z-Thr-Pro-Lys(BOC)-Ala-O$^t$Bu

In 40 ml. of methanol was dissolved 2.12 g. of Z-Pro-Lys(BOC)-Ala-O$^t$Bu and catalytic reduction was carried out with Pd-black as a catalyst for 3 hours. The catalyst was filtered off and the solvent was distilled off under reduced pressure.

The residue was dissolved in 20 ml. of dioxane. On the other hand, 977 mg. of Z-Thr-OH and 806 mg. of HONB were dissolved in 10 ml. of ethyl acetate-dioxane (1:1) and under cooling with ice, 800 mg. of DCC was added. The mixture was stirred for 6 hours and the formed DC-urea was filtered off and the filtrate was added to the above dioxane solution. The mixture was stirred for 16 hours. The solvent was distilled off under reduced pressure and the residue was dissolved in 150 ml. of ethyl acetate. The solution was washed with 0.5N sulfuric acid and 4% aqueous sodium hydrogen carbonate. After washing with water, it was dried over anhydrous sodium sulfate and the solvent was distilled off under reduced pressure. To the residue was added petroleum benzin and the resulting powder was collected. Yield 2.3 g. (93%); melting point: 64-67° C; $[\alpha]_D^{23}$ −75.58°(c=0.995, methanol).

Elemental analysis, for $C_{35}H_{55}O_{10}N_5$ Calcd. C, 59.55; H, 7.85; N, 9.92 Found C, 59.25; H, 7.99; N, 9.65

(d) Preparation of Z-Phe-Phe-Tyr-Thr-Pro-Lys(BOC)-Ala-O$^t$Bu

In 70 ml. of methanol was dissolved 1.41 g. of Z-Thr-Pro-Lys(BOC)-Ala-O$^t$Bu and catalytic reduction was carried out with Pd-black as a catalyst for 2 hours. The catalyst was filtered off and the solvent was distilled off under reduced pressure. The residue was dissolved in 10 ml. of DMF, followed by the addition of 1.1 g. of Z-Phe-Phe-Tyr-OH and 720 mg. of HONB. Under cooling with ice, 618 mg. of DCC was added and the mixture was stirred for 20 hours. The solvent was distilled off under reduced pressure and the residue was treated with ethyl acetate-ether (1:1). The resulting powder was collected by filtration and crystallized from ethanol. Yield 2.1 g. (100%); melting point: 160°-163.5° C; $[\alpha]_D^{23}$ −63.73°(c=1.05%, methanol)

Elemental analysis, for $C_{62}H_{80}O_{16}N_8$ Calcd. C, 62.09; H, 7.23; N, 9.34 Found C, 62.02; H, 7.14; N, 9.64

(e) Preparation of Z-Arg($NO_2$)-Gly-Phe-Phe-Tyr-Thr-Pro-Lys(BOC)-Ala-O$^t$Bu

In 30 ml. of methanol was dissolved 2.32 g. of Z-Phe-Phe-Tyr-Thr-Pro-Lys(BOC)-Ala-O$^t$Bu, and catalytic reduction was carried out with Pd-black as a catalyst for 3 hours. The catalyst was filtered off and the methanol was distilled off. The residue was dissolved in 5 ml. of DMF. To this solution was added 1.26 g. of Z-Arg($NO_2$)-Gly-ONB and the mixture was stirred at room temperature for 20 hours. The DMF was distilled off under reduced pressure and 50 ml. of water was added to the residue. The resulting powder was collected by filtration and reprecipitated twice from DMF-water. Yield 2.5 g. (88%); melting point: 138°-141° C(decomp.); $[\alpha]_D^{24} - 32.4°(c = 0.99\%, DMF)$ Elemental analysis, for $C_{70}H_{96}O_{18}N_{14}$ Calcd. C, 59.14; H, 6.81; N, 13.80 Found C, 58.82; H, 6.80; N, 13.66

(f) Preparation of β-Ala-Arg-Gly-Phe-Phe-Tyr-Thr-Pro-Lys-Ala-OH

In 30 ml. of a mixture of methanol and glacial acetic acid (2:1) was dissolved 710 mg. of Z-Arg(NO₂)-Gly-Phe-Phe-Tyr-Thr-Pro-Lys(BOC)-Ala-O'Bu and catalytic reduction was carried out with palladium black as a catalyst for 8 hours. The catalyst was filtered off and the filtrate was concentrated to dryness under reduced pressure. The residue was dissolved in 10 ml. of water and the solution was passed through a column (130 ml.) of carboxymethyl-cellulose. Gradient elution was carried out with 0.005M aqueous ammonium acetate and 0.2M aqueous ammonium acetate (800 ml. each). The fractions from 913 ml. to 1190 ml. were pooled and lyophilized to obtain 350 mg. of a white fluffy product.

This powder was dissolved in 8 ml. of DMF, and 41 mg. of p-toluenesulfonic acid monohydrate was added. This was followed by the addition of 82 mg. of BOC-β-Ala-ONB and the mixture was stirred for 16 hours. The DMF was distilled off under reduced pressure, and 3 ml. of trifluoroacetic acid was added to the residue. The mixture was shaken for 30 minutes and the trifluoroacetic acid was distilled off. The residue was dissolved in 10 ml. of water and passed through a column (1.0 × 10cm) of Amberlite IRA-410 (acetate-form), whereby the compound was converted to the acetate. The eluate was lyophilized and applied on a column (2.2 × 17 cm) of carboxymethyl-cellulose. Gradient elution was carried out with 0.005M aqueous ammonium acetate (500 ml.) and 0.2M aqueous ammonium acetate (500 ml.). The fractions from 430 ml. to 500 ml. were pooled and lyophilized to obtain 250 mg. of a white fluffy product. $[\alpha]_D^{24} - 58.8°(c = 0.5\%,$ water) Amino acid analysis: Lys, 1.00; Arg, 1.04; Thr, 1.00; Pro, 1.04; Gly, 1.04; Ala, 1.04; Tyr, 0.89; Phe, 2.00; β-Ala, 0.93(peptide content 72%).

EXAMPLE 23

Production of Gly-Arg-Gly-Phe-Phe-Tyr-Pro-Lys-Ala-OH

The procedure of Example 22-f was repeated except that BOC-β-Ala-ONB was replaced with BOC-Gly-ONB to obtain 214 mg. of the above-indicated compound as a white fluffy product. $[\alpha]_D^{23} - 59.2°(c = 0.4\%,$ water) Amino acid analysis: Lys, 102; Arg, 1.00; Thr, 1.00; Pro, 1.01; Gly, 2.00; Ala, 1.03; Tyr, 0.87; Phe, 2.04 (peptide content 78%)

EXAMPLE 24

Production of Leu-Arg-Gly-Phe-Phe-Tyr-Gly-NH₂

(a) Preparation of Z-Leu-Arg(Tos)-Gly-Phe-Phe-Tyr(Bzl)-Gly-resin

In the reaction vessel of a solid-phase peptide synthesizer (Simadzu APS-800) was put 4.04 g. of BOC-Gly-resin (containing 1.75 m mol of Gly), which was swollen with dichloromethane for 20 hours. Thereafter, according to the method of Merrifield, there were introduced BOC-Tyr(Bzl)-OH BOC-Phe-OH, BOC-Phe-OH, BOC-Gly-OH, Aoc-Arg(Tos)-OH and Z-Leu-OH in the order mentioned. DCC was used as a condensing agent and each amino acid was used in four equivalents, the removal of BOC-groups being effected with trifluoroacetic acid-dichloromethane (1:1). The resin was taken out from the reaction vessel and washed with dichloromethane, DMF, methanol and acetic acid, followed by drying. The procedure yielded 5.07 g. of the above-indicated resin.

(b) Preparation of Z-Leu-Arg(Tos)-Gly-Phe-Phe-Tyr(Bzl)-Gly-NH₂

In 50 ml. of 17% ammonia-methanol was suspended 4.41 g. of the resin prepared in a) and, under sealing, the suspension was stirred at room temperature for 48 hours. The resin was filtered off and washed well with DMF. The filtrate and washings were pooled and the solvent was distilled off under reduced pressure. To the oily residue was added ethyl ether and the resulting powder was collected by filtration and washed well with ether. Yield 950 mg.

(c) Preparation of Leu-Arg-Gly-Phe-Phe-Tyr-Gly-NH₂

In 10 ml. of anhydrous hydrogen fluoride were dissolved 500 mg. of the crude protected peptide-amide prepared in b) and 0.5 ml. of anisole and the solution was stirred at 0° C for 60 minutes. The hydrogen fluoride was distilled off and the residue was dissolved in 50 ml. of water. The solution was extracted twice with 20 ml. of ethyl ether and the aqueous layer was passed through a column (2 × 10 cm) of Amberlite IRA-410(acetate-form) and lyophilized. The product was passed through a column (2.3 × 17 cm) of carboxymethyl-cellulose and gradient elution was carried out with 0.005M aqueous ammonium acetate (400 ml.) and 0.2M aqueous ammonium acetate (400 ml.). The fractions from 490 ml. to 550 ml. were pooled and lyophilized. The procedure yielded 167 mg. of the above-indicated compound as a white fluffy product. Amino acid analysis: Ar, 1.02, Gly, 2.00; Leu, 1.03; Tyr, 0.89; Phe, 2.08 (peptide content 84%).

EXAMPLE 25

Production of β-Ala-Arg-Gly-Phe-Phe-Tyr-Ala-Gly-NH₂

(a) Preparation of Z-β-Ala-Arg(Ros)-Gly-Phe-Phe-Tyr(Bzl)-Ala-Gly-resin

In the reaction vessel of a Simadzu APS-800 synthesizer was put 3.03 g. of BOC-Gly-resin(Gly content 1.32 mM), which was then swollen with dichloromethane. Then, BOC-Ala-OH, BOC-Tyr(Bzl)-OH, BOC-Phe-OH, BOC-Phe-OH, BOC-Gly-OH, Aoc-Arg(Tos)-OH and Z-β-Ala-OH were introduced in the order mentioned by the symmetric anhydride process [See Hoppe-Seyler's, Z.Physiol. Chem.353, 1973(1972)]. The removal of BOC in each step was made by means of 50% trifluoroacetic acid-dichloromethane.

Moreover, in each step, the unreacted amino groups were acylated with acetic anhydride. After all the amino acids had been introduced, the resin was washed with ethanol, DMF, dichloromethane, acetic acid and methanol, followed by drying under reduced pressure. The procedure yielded 3.70 g. of peptide resin.

(b) Preparation of Z-β-Ala-Arg(Tos)-Gly-Phe-Phe-Tyr(Bzl)-Ala-Gly-NH₂

In 50 ml. of 17% ammonia-methanol was suspended 3.28 g. of the peptide resin prepared in a) and, under sealing, the suspension was stirred at room temperature for 40 hours. The resin was filtered off and washed with 50 ml. of DMF. The filtrate and washings were pooled and concentrated to dryness under reduced pressure.

To the residue was added ether and the resulting powder was collected by filtration and dried. The procedure yielded 433 mg. of the crude protected peptide-amide.

(c) Preparation of β-Ala-Arg-Gly-Phe-Phe-Tyr-Ala-Gly-NH$_2$

In a mixture of 8 ml. of anhydrous hydrogen fluoride and 0.3 ml. of anisole was dissolved 310 mg. of the crude protected peptide-amide prepared b) above and the solution was stirred at 0° C for 60 minutes.

The hydrogen fluoride was distilled off under reduced pressure and the residue was dissolved in 50 ml. of water. The solution was extracted twice with 10 ml. of ether. The aqueous layer was passed through a column (1 × 10 cm) of Amberlite IRA-410 (acetate-form), which was washed with water. The effluent and washings were combined and the combined solution was lyophilized. The product was dissolved in 10 ml. of water and the solution was passed through a column (2.3 × 17 cm) of carboxymethyl-cellulose. Gradient elution was carried out with 0.005 M and 0.2M aqueous solutions of ammonium acetate (400 ml. each). The fractions from 495 ml. to 540 ml. were pooled and lyophilized to obtain 134 mg. of the above-indicated product. $[\alpha]_D^{23} - 19.62°(c=0.53\%, water)$ Amino acid analysis: Arg, 1.05; Gly, 1.95; Ala, 1.00; Tyr, 0.86; Phe, 1.98; '-Ala, 1.02(peptide content 84%). Elemental analysis, for $C_{43}H_{58}O_9N_{12}.2C_2H_4O_2.4H_2O$ Calcd. C, 52.31; H, 6.91; N, 15.57 Found: C, 52.40; H, 6.55; N, 15.65

EXAMPLE 26

Production of α,γ-Dab-Arg-Gly-Phe-Phe-Tyr-Ala-Gly-NH$_2$

The procedure of Example 25 was repeated except that, as the amino acid to be finally introduced, di-Z-α,γ-Abu-OH was used in place of Z-β-Ala-OH. The procedure provided the above-indicated compound as a white fluffy product. $[\alpha]_D^{21}$ 20.3°(c=0.2%, water)

Amino acid analysis: Arg, 1.00; Gly, 1.89; Ala, 1.02; Tyr, 0.88; Phe, 2.00; α,γ-Abu, 1.04(peptide content 81.5%)

EXAMPLE 27

Production of Gly-Arg-Gly-Phe-Phe-NH$_2$ (a) Preparation of Z-Gly-Arg(NO$_2$)-Gly-Phe-Phe-NH$_2$ To 0.80 g. of Z-Arg(NO$_2$)-Gly-Phe-Phe-NH$_2$ was added 8 ml. of 25% HBr-acetic acid and the mixture was shaken well at room temperature for 45 minutes. To the reaction mixture was added 100 ml. of ether and the resulting powder was collected by filtration and dried over sodium hydroxide pellets in a desiccator under reduced pressure for 2 days. The dried product was dissolved in 10 ml. of DMF and the solution was neutralized with triethylamine. To the solution was added 0.43 g. of Z-Gly-ONB and the mixture was stirred for 10 hours.

To the solution was added 7 ml. of water, whereupon an oil separated. After the supernatant was removed by decantation, 50 ml. of water was added. The resulting powder was collected by filtration and dried. This product was purified by reprecipitation with DMF-ethyl acetate. Yield 0.66 g. (77%); melting point: 119°-122° C; $[\alpha]_D^{21}$ 24.6° (c=1.01%, DMF).

Elemental analysis, $C_{36}H_{44}O_9N_{10}.H_2O$ Calcd. C, 55.51; H, 5.95; N, 17.99 Found C, 55.95; H, 5.90; N, 17.73

(b) Preparation of Gly-Arg-Gly-Phe-Phe-NH$_2$

In 30 ml. of acetic acid was dissolved 500 mg. of Z-Gly-Arg(NO$_2$)-Gly-Phe-Phe-NH$_2$, and catalytic reduction was carried out in hydrogen streams with Pd-black as a catalyst for 7 hours. The catalyst was filtered off and the acetic acid was distilled off under reduced pressure. The residue was dissolved in 10 ml. of water and the solution was passed through a column (1.8 × 10 cm) of carboxymethyl-cellulose.

Elution was carried out by the linear gradient method using 0.1M aqueous ammonium acetate (700 ml.) and 1M aqueous ammonium acetate (700 ml.). The fractions from 410 ml. to 515 ml. were pooled and lyophilized to obtain 307 mg.(65%) of white fluffy product. $[\alpha]_D^{22} - 17.7°(c=0.48\%, water)$ Amino acid analysis(-hydrolysis with HCl): Arg, 1.15; Gly, 2.00; Phe, 2.00(peptide content 84.6%) Elemental analysis, for $C_{28}H_{39}O_5N_9.2C_2H_4O_2.2H_2O$ Calc. C, 52.09; H, 6.97; N, 17.09 Found C, 52.05; H, 6.85; N, 17.22

EXAMPLE 28

Production of D-Ala-Arg-Gly-Phe-Phe-NH$_2$ (a) Preparation of Z-D-Ala-Arg(NO$_2$)-Gly-Phe-Phe-NH$_2$ In 8 ml. of 25% HBr-acetic acid was dissolved 0.80 g. of Z-Arg(NO$_2$)-Gly-Phe-Phe-NH$_2$ and the solution was shaken at room temperature for 40 minutes. To the mixture was added 100 ml. of ethyl ether, whereupon precipitates formed. The precipitates were collected by filtration, washed with ether and dried. This dried product was dissolved in 10 ml. of DMF and the solution was neutralized with triethylamine, followed by the addition of 0.51 g. of Z-D-Ala-ONB. The mixture was stirred for 8 hours. The DMF was distilled off under reduced pressure, and 50 ml. of water was added to the residue.

The resulting powder was collected by filtration. After drying, the powder was washed with hot ethyl acetate and reprecipitated from DMF-ethyl acetate. Yield 0.799 g. (92%); melting point: 223–225° C; $[\alpha]_D^{21} - 22.3°(c=0.98\%, DMF)$.

Elemental analysis, for $C_{37}H_{46}O_9N_{10}.\frac{1}{2}H_2O$ Calcd. C, 56.69; H, 6.04; N, 17.87 Found C, 56.38; H, 6.07; N, 17.98

(b) Preparation of D-Ala-Arg-Gly-Phe-Phe-NH$_2$

In 30 ml. of acetic acid was dissolved 600 mg. of Z-D-Ala-Arg(NO$_2$)-Gly-Phe-Phe-NH$_2$ and catalytic reduction was carried out with Pd-black as a catalyst for 7 hours. The catalyst was filtered off and the solvent was distilled off under reduced pressure. The residue was dissolved in 10 ml. of water and the solution was passed through a column (1.8 × 11 cm) of carboxymethyl-sephadex.

Linear gradient elution was carried out with 0.1 M aqueous ammonium acetate (700 ml.) and 1M aqueous ammonium acetate (700 ml.), whereupon the above-indicated compound emerged in fractions from 350 ml. to 450 ml. These fractions were pooled and lyophilized. The procedure yielded 400 mg. (73%) of a white fluffy product. $[\alpha]_D^{22} - 22.2°(c=0.51\%, water)$:

Amino acid analysis: Arg, 1.01; Gly, 1.03; Ala, 1.00; Phe, 1.99 (peptide content 82.3%)

Elementaly analysis, for $C_{29}H_{41}O_5N_9.2C_2H_4O_2.2H_2O$ Calcd. C, 52.72; H, 7.11; N, 16.77 Found C, 52.66; H, 6.92; N, 16.82

EXAMPLE 29

Production of Phe-Arg-Gly-Phe-Phe-NH$_2$ (a) Preparation of Z-Phe-Arg(NO$_2$)-Gly-Phe-Phe-NH$_2$ In 10 ml. of 25% HBr-acetic acid was dissolved 800 mg. of Z-Arg(NO$_2$)-gly-Phe-Phe-NH$_2$ and the solution was shaken for 50 minutes. To the solution was added 80 ml. of ether and the resulting precipitates were collected by filtration, dried and dissolved in 10 ml. of DMF. The solution was neutralized with triethylamine, followed by the addition of 700 mg. of Z-Phe-OPCP(pentachlorophenyl ester). The mixture was stirred for 10 hours and 50 ml. of 1N aqueous ammonia was added. The oily layer was taken by decantation and water was added to the oily substance. The resulting powder was collected by filtration and dried. Following the addition of 50 ml. of ethyl acetate to the powder, the mixture was heated and the powder was collected by filtration when hot. The powder was purified by reprecipitation from DMF-ethyl acetate. Yield 805 mg.(92%); $[\alpha]_D^{21} - 29.0°(c=1.0\%$, DMF). Elemental analysis, for C$_{43}$H$_{50}$O$_9$N$_{10}$·½H$_2$O Calcd. C, 60.06; H, 5.98; N, 16.29 Found C, 60.32; H, 6.02; N, 16.10

(b) Preparation of Phe-Arg-Gly-Phe-Phe-NH$_2$

In 6-ml. of anhydrous hydrogen fluoride was dissolved 500 mg. of Z-Phe-Arg(NO$_2$)-Gly-Phe-Phe-NH$_2$ and the solution was stirred at $-10°$ C for 40 minutes. The hydrogen fluoride was distilled off and the residue was dissolved in 10 ml. of water. The solution was passed through a column (0.9 × 15 cm) of Amberlite IRA-410(acetate-form) which was washed with water. The effluent was combined with the washings and the combined solution was lyophilized. The procedure yielded 402 mg. of the above-indicated compound. Amino acid analysis: Arg, 1.01; Gly, 0.98; Phe, 2.94 (peptide content 86.2%).

EXAMPLE 30

Production of Leu-Arg-Gly-Phe-Phe-Tyr-NH$_2$ (a) Preparation of Z-Arg(NO$_2$)-Gly-Phe-Phe-Tyr-NH$_2$ In 100 ml. of DMF was dissolved 12.2 g. of Z-Phe-Phe-Tyr-NH$_2$ and catalytic reduction was carried out with Pd-black as a catalyst for 5 hours. The catalyst was filtered off, and 8.6 g. of Z-Arg(NO$_2$)-Gly-OH and 4.3 g. of HONB were added.

Under cooling with ice, 4.95 g. of DCC was then added. The mixture was stirred for 12 hours. The formed DC-urea was filtered off and 1 l. of water was added to the filtrate. The resulting gels were collected by filtration and reprecipitated from methanol and water. Yield 16.25 g.(91.8%); melting point: 181–184° C; $[\alpha]_D^{24} - 16.0°(c=1.01\%$, DMF).

Elemental analysis, for C$_{43}$H$_{50}$O$_{10}$N$_{10}$·H$_2$O Calcd. C, 58.35; H, 5.92; N, 15.83 Found C, 58.02; H, 5.98; N, 15.66

(b) Preparation of Arg-Gly-Phe-Phe-Tyr-NH$_2$

In 30 ml. of acetic acid was dissolved 600 mg. of Z-Arg(NO$_2$)-Gly-Phe-Phe-Tyr-NH$_2$, and catalytic reduction was carried out with Pd-black as a catalyst for 9 hours. The catalyst was filtered off and the solvent was distilled off under reduced pressure. The residue was dissolved in 15 ml. of water and purified by means of a column (1.3 × 11 cm) of carboxymethyl sephadex. Linear gradient elution was carried out with 0.1M aqueous ammonium acetate (500 ml.) and 1M aqueous ammonium acetate (500 ml.). The fractions from 250 ml. to 420 ml. were pooled and lyophilized. Yield 416 mg.(72.5%). $[\alpha]_D^{25} - 7.6°(c=0.49\%$, water)

Elemental analysis, for C$_{35}$H$_{47}$O$_6$N$_9$·2C$_2$H$_4$O$_2$·2H$_2$O Calcd. C, 55.37; H, 7.03; N, 14.90 Found C, 55.81; H, 6.83; N, 14.78

Amino acid analysis: Arg, 1.02; Gly, 1.00; Tyr, 0.91; Phe, 2.02 (peptide content 82.5%)

(c) Preparation of Z-Leu-Arg(NO$_2$)-Gly-Phe-Phe-Tyr-NH$_2$

To 700 mg. of Z-Arg(NO$_2$)-Gly-Phe-Phe-Tyr-NH$_2$ was added 0.2 ml. of anisole, followed by the addition of 7 ml. of 25% HBr-acetic acid. The mixture was shaken at room temperature for 40 minutes, followed by the addition of 100 ml. of ethyl ether. The resulting precipitates were collected by filtration dried and dissolved in 10 ml. of DMF. The solution was neutralized with triethylamine, followed by the addition of 344 mg. of Z-Leu-Osu(N-hydroxysuccinimide ester). The mixture was stirred for 12 hours. The DMF was distilled off under reduced pressure, and 50 ml. of water was added to the residue. The resulting powder was collected by filtration and purified by reprecipitation from methanol and water. Yield 560 mg. (70.9%); melting point: 193–195° C; $[\alpha]_D^{22} - 18.9°(c=1.13\%$, DMF)

Elemental analysis, for C$_{49}$H$_{61}$O$_{11}$N$_{11}$·H$_2$O Calcd. C, 58.96; H, 6.36; N, 15.44 Found C, 58.72; H, 6.22; N, 15.36

(d) Preparation of Leu-Arg-Gly-Phe-Phe-Tyr-NH$_2$

In 30 ml. of acetic acid was dissolved 400 mg. of Z-Leu-Arg(NO$_2$)-Gly-Phe-Phe-Tyr-NH$_2$ and catalytic reduction was carried out with Pd-black as a catalyst for 10 hours. The catalyst was filtered off and the solvent was distilled off under reduced pressure. The residue was dissolved in 5 ml. of water and the solution was passed through a column (2.6 × 22 cm) of carboxylmethyl-cellulose.

Gradient elution was carried out with 0.005M aqueous ammonium acetate (700 ml.) and 0.2M aqueous ammonium acetate (700 ml.). The fractions from 830 ml. to 910 ml. were pooled and lyophilized. Yield 217 mg.(55.5%); $[\alpha]_D^{22} - 14.9°(c=0.47\%$, water). Calcd. C, 55.43; H, 7.24; N, 14.37 Found C, 55.71; H, 7.12; N, 14.81 Amino acid analysis: Arg, 1.03; Gly, 1.00; Leu, 1.00; Phe, 2.00; Tyr, 0.85 (peptide content 78.0 %)

EXAMPLE 31

Production of α-Abu-Arg-Gly-Phe-Phe-Tyr-NH$_2$

The procedure of Example 30 was repeated except that Z-α-Abu was used in place of Z-leu to obtain the above-indicated compound. $(\alpha)_D^{22} - 13.6°(c=0.32$ %, water); Amino acid analysis: Arg, 1.02; Gly, 0.98; α-Abu, 1.04; Phe, 2.00; Tyr, 0.92(peptide content 81 %).

EXAMPLE 32

Production of Nle-Arg-Gly-Phe-Tyr-NH$_2$

The procedure of Example 30 was repeated except that Z-Nle was used in place of Z-leu to obtain the above-indicated compound. $(\alpha)_D^{24} - 14.3°(c=0.4$ %, water)

Amino acid analysis: Arg, 1.00; Gly, 0.97; Nle, 1.04; Phe, 2.03; Tyr, 0.91 (peptide content 84 %).

EXAMPLE 33

Production of Val-Arg-Gly-Phe-Phe-Tyr-NH$_2$

In 10 ml. of DMF was dissolved 400 mg. of the Arg-Gly-Phe-Phe-Tyr-NH₂ diacetate prepared in Example 30-b), followed by the addition of 300 mg. of Z-Val-ONB. The solution was neutralized with triethylamine and stirred for 10 hours. To the solution was added 50 ml. of ether and the resulting precipitates were collected by filtration, washed with ethyl acetate and dried. This product was dissolved in 30 ml. of acetic acid-water (1:1) and catalytic reduction was carried out with Pd-black as a catalyst for 4 hours. The catalyst was filtered off and the filtrate was concentrated to dryness. The residue was dissolved in 10 ml. of water and purified by chromatography in the same manner as Example 30-c). Yield 360 mg.; $(\alpha)_D^{22} -13.7°$ (c=0.5 %, water) Amino acid analysis: Arg, 1.02; Gly, 1.00; Val, 0.97; Phe, 2.04; Tyr, 0.97 (peptide content 86.2 %)

EXAMPLE 34

Production of β-Ala-Arg-Gly-Phe-Phe-NH₂

(a) Production of Z-Arg(NO₂)-Gly-OEt

In 200 ml. of tetrahydrofuran was dissolved 70.7 g. of Z-Arg(NO₂)-OH and, under cooling with ice, 40.5 g. of 2,4-dinitrophenol and 45.4 g. of DCC were added. The mixture was stirred for 4 hours. On the other hand, 30.7 g. of Gly-OEt·HCl was suspended in 200 ml. of tetrahydrofuran and, under cooling with ice, the suspension was neutralized with 30.8 ml. of triethylamine. The formed dicyclohexylurea was filtered off, and the active ester solution prepared above was added to the filtrate, followed by stirring overnight. The solution was concentrated and the residue was dissolved in 500 ml. of ethyl acetate. The solution was washed with a saturated aqueous solution of sodium hydrogen carbonate (200 ml. × 3), with 1N hydrochloric acid (200 ml. × 3) and, then, with a saturated aqueous solution of sodium chloride (200 ml. × 3), followed by drying over anhydrous sodium sulfate. The solution was concentrated and crystallized from ethyl acetate-petroleum benzin. The crystals were recovered by filtration and recrystallized from ethyl acetate-petroleum benzin. Yield 70.0 g. (79.8 %) melting point: 109°–110° C; $[\alpha]_D^{26.5} -3.4°$ (c=1 %, DMF); elemental analysis; calcd. for $C_{18}H_{26}O_7N_6$: C, 49.31; H, 5.98; N, 19.17; found: C, 49.26: H, 5,79; N, 18.55.

(b) Production of Z-Arg(NO₂)-Gly-OH

In 100 ml. of acetone was suspended 20.0 g. of Z-Arg(NO₂)-Gly-OEt and, under cooling with ice, 64 ml. of 1n aqueous sodium hydroxide solution was added. The mixture was stirred at room temperature for 2 hours.

After the excess alkali was neutralized with hydrochloric acid, the solution was concentrated under reduced pressure and 100 ml. of water was added to the residue. The insolubles were filtered off. The filtrate was made acidic with hydrochloric acid and the resultant crystals were recovered by filtration. Yield 18.3 g. (93.7 %); melting point: 103–105° C; $[\alpha]_D^{22} -25.9°$ (c=0.9 %, DMF); elemental analysis: calcd. for $C_{16}H_{22}O_7N_6.H_2O$: C, 44.86; H, 5.65; N, 19.62; found: C, 44.48; H, 5.35; N, 19.53

(c) Production of Z-Arg(NO₂)-Gly-Phe-Phe-NH₂

In a mixture of 60 ml. of DMF and 40 ml. of methanol was dissolved 8.91 g. of Z-Phe-Phe-NH₂ and catalytic hydrogenation was carried out for 14 hours in the presence of palladium black. The catalyst was filtered off and the solvent was distilled off under reduced pressure. The residue was dissolved in 30 ml. of DMF. On the other hand, 6.80 g. of Z-Arg(NO₂)-Gly-OH was added to 50 ml. of tetrahydrofuran and, under cooling with ice, 3.23 g. of HONB and 3.71 g. of DCC were added, followed by stirring for 5 hours. The formed dicyclohedxylurea was filtered off and the above amine component (H-Phe-Phe-NH₂) was added. The mixture was stirred overnight. After the solvent was distilled off under reduced pressure, 100 ml. of water was added to the residue and the resulting powder was collected by filtration.

After drying, the product was washed with ethyl acetate and recrystallized from thanol-ethyl acetate. Yield 8.34 g. (72.7%); melting point: 112°–113° C, $[\alpha]_D^{22} -21.6°$ (c=1%, DMF); elemental analysis: calcd. for $C_{34}H_{41}O_8N_9.H_2O$ : C, 56.58; H, 6.01; N, 17.47; found: C, 56.57; H 5.72; N, 17.40.

(d) Production of Z-β-Ala-ONB

In 40 ml. of tetrahydrofuran were dissolved 3.35 g. of Z-β-Ala-OH and 3.23 g. of HONB and, after cooling with ice, 3.71 g. of DCC was added. The mixture was stirred overnight and the formed dicyclohexylurea was filtered off. The solvent was distilled off under reduced pressure and petroleum benzin was added. The resultant crystals were removed by filtration and recrystallized from acetontrile. Yield 3.83 g. (66.4%); melting point: 125–126° C; elemental analysis: calcd. for $C_{20}H_{20}O_6N_2$: C, 62.49; H, 5.24; N, 7.29; found: C, 62.52; H, 5.18; N, 7.29

(e) Production of Z-β-Ala-Arg(NO₂)-Gly-Phe-Phe-NH₂

To 1.06 g. of Z-Arg(NO₂)-Gly-Phe-Phe-NH₂ was added 10 ml. of 25 % HBr-acetic acid and, after shaking at room temperature for 40 minutes, ethyl ether was added. The resultant precipitate was recovered by filtration, dried under reduced pressure in a desiccator over sodium hydroxide and dissolved in 10 ml. of DMF. After cooling, the solution was neutralized with 0.84 ml. of triethylamine and then, 0.69 g. of Z-β-Ala-ONB was added. The mixture was stirred overnight and the solvent was distilled off under reduced pressure, followed by addition of 50 ml. of water. The resultant powder was dried, washed with ethyl acetate and reprecipitated from water-dioxane-ethyl acetate. Yield 0.98 g. (83.3%); melting point: 161°–163° C; $[\alpha]_D^{21.5} -20.9°$ (c=0.9%, DMF); elemental analysis: calcd. for $C_{37}H_{46}O_9N_{10}.\frac{1}{2}H_2O$: C, 56.69; H, 6.04; N, 17.89; found: C, 56.84; H, 5.88; N, 17.50

(f) Production of β-Ala-Arg-Gly-Phe-Phe-NH₂

In 40 ml. of acetic acid was dissolved 800 mg. of Z-β-Ala-Arg(NO₂)-Gly-Phe-Phe-NH₂ together with Pd as a catalyst, and catalytic reduction was carried out for 14 hours. The catalyst was filtered off and the solvent was distilled off under reduced pressure. The residue was applied on a column (2.5 cm × 9 cm) of carboxymethyl-sephadex, and elution was carried out by the linear gradient method from 0.01 N aqueous ammonium acetate (700 ml.) through 1N aqueous ammonium acetate (700 ml.).

The fractions from 780 ml. to 990 ml. were pooled and lyophilized. Yield 500 mg. (66%); $[\alpha]_D^{23.5} -13.9°$ (c=0.5%, water); elemental analysis: calcd. for $C_{29}H_{41}O_5N_2.2C_2H_4O_2.H_2O$ : C, 54.00; H, 7.01; N, 17.18; Found: C, 53.75; H, 7.07; N, 17.15; amino acid analysis: Arg, 1.00(1), Gly, 1.00(1), Phe, 2.00(2) (the figures in parentheses denote theoretical values; the same applies hereinafter). Peptide content 76%.

EXAMPLE 35

Production of γ-Abu-Arg-Gly-Phe-Phe-NH$_2$ (a) Production of Z-γ-Abu-ONB

In 40 ml. of tetrahydrofuran were dissolved 4.75 g. of Z-γ-Abu-OH and 394 g. of HONB and, after cooling with ice, 4.54 g. of DCC was added. The mixture was stirred for 6 hours and the formed dicyclohexylurea was filtered off. The solvent was then distilled off under reduced pressure and 30 ml. of ethyl ether was added to the residue, followed by addition of a small amount of water. The resultant crystals were recovered by filtration. Yield 6.0 g. (75.3%); melting point 66–69° C; elemental analysis: calcd. for $C_{21}H_{22}O_6N_2$: C, 63.31; H, 5.57; N, 7.03; found: C, 63.39; H, 5.42; N, 7.06.

(b) Production of Z-γ-Abu-Arg(NO$_2$)-Gly-Phe-Phe-NH$_2$

In the same manner as Example 34-e), 0.53 g. of Z-Arg(NO$_2$)-Gly-Phe-Phe-NH$_2$ was treated with HBr-acetic acid and dissolved in 15 ml. of DMF. After the solution was neutralized with triethylamine, 0.44 g. of Z-γ-Abu-ONB was added. The mixture was stirred overnight. The solvent was distilled off under reduced pressure and water was added. The resultant powder was recovered by filtration and dried well.

It was washed with ethyl acetate and reprecipitated from ethanol-water. Yield 0.38 g. (65%); melting point: 167°–170° C; $[\alpha]_D^{26.5} -21.2°$ (c=1.0%, DMF); elemental analysis: calcd. for $C_{38}H_{48}O_9N_{10} \cdot \frac{1}{2}H_2O$ : C, 57.20; H, 6.19; N, 17.56; found: C, 57.14; H, 6.10; N, 17.56.

(c) Production of γ-Abu-Arg-Gly-Phe-Phe-NH$_2$

In 30 ml. of acetic acid was dissolved 300 mg. of Z-γ-Abu-Arg(NO$_2$)-Gly-Phe-Phe-NH$_2$ and, with Pd as a catalyst, catalytic reduction was carried out for 6 hours.

After the catalyst was filtered off, the solvent was distilled off under reduced pressure and the residue was applied on a column (1.8 cm × 10 cm) of carboxymethyl-sephadex. Then, elution was carried out by the linear gradient method from 0.005N aqueous ammonium acetate (350 ml.) through 1N aqueous ammonium acetate (350 ml.) and the fractions from 290 ml. to 340 ml. were pooled and lyophilized. Yield 180 mg. (63%); $[\alpha]_D^{26} -15.0°$ (c=0.5%, water); elemental analysis: calcd. for $C_{30}H_{43}O_5N_9 \cdot 2C_2H_4O_2 \cdot 3/2H_2O$ : C, 53.95; H, 7.19; N, 16.66; found: C, 53,93; H, 7.29; N, 16,34; amino acid analysis: Arg 1.00(1), Gly 1.00(1), Phe 1.94(2); peptide content 76%.

EXAMPLE 36

Production of δ-Aval-Arg-Gly-Phe-Phe-NH$_2$ (a) Production of Z-δ-Aval-Arg(NO$_2$)-Gly-Phe-Phe-NH$_2$ In the same manner as Example 34-e), 0.80 g. of Z-Arg(NO$_2$)-Gly-Phe-Phe-NH$_2$ was treated with HBr-acetic acid and dissolved in 10 ml. of DMF. The solution was neutralized with triethylamine. On the other hand, 0.30 g. of Z-δ-Aval-OH and 0.24 g. of HONB were dissolved in 5 ml. of tetrahydrofuran.

While cooling with ice, 0.27 g. of DCC was added and the mixture was stirred for 3 hours. The dicyclohexylurea was filtered off and the filtrate was added to the above amine component [H-δ-Acal-Arg(NO$_2$)-Gly-Phe-NH$_2$], followed by stirring overnight. The solvent was distilled off under reduced pressure and water was added. The resultant powder was recovered by filtration and dried well. It was washed with ethyl acetate and reprecipitated from DMF-ethyl acetate. Yield 0.62 g. (70 %); melting point: 154°–157° C; $[\alpha]_D^{23} -13.0°$ (c=1.0%, DMF); elemental analysis: calcd. for $C_{39}H_{50}O_9N_{10} \cdot \frac{1}{2}H_2O$ : C, 57.69; H, 6.33; N, 17.25; found: C, 57.84; H, 6.42; N, 16.86.

(b) Production of δ-Aval-Arg-Gly-Phe-Phe-NH$_2$

In 30 ml. of acetic acid was dissolved 500 mg. of Z-Aval-Arg(NO$_2$)-Gly-Phe-Phe-NH$_2$ and, with Pd as a catalyst, catalytic reduction was carried out for 5 hours. After the catalyst was filtered off, the solvent was distilled off under reduced pressure. The residue was applied on a column of carboxymethyl-sephadex (1.8 cm × 9 cm) and elution was carried out by the linear gradient method from 0.1N aqueous ammonium acetate (500 ml.) through 1N aqueous ammonium acetate (500 ml.). The fractions from 290 ml. to 370 ml. were pooled and lyophilized. Yield 290 mg.(61%); $[\alpha]_D^{23} -12.6°$ (c=0.5%, water); elemental analysis: calcd. for $C_{31}H_{45}O_5N_9 \cdot 2C_2H_4O_2 \cdot 3/2H_2O$ : C, 54.53; H, 7.32; N, 16.36; found: C, 54.34; H, 7.35; N, 16.20; amino acid analysis: Arg, 1.11(1), Gly, 1.00(1), Phe, 2.04(2); peptide content: 81.4%

EXAMPLE 37

Production of ε-Acap-Arg-Gly-Phe-Phe-NH$_2$ (a) Production of Z-ε-Acap-Arg(NO$_2$)-Gly-Phe-Phe-NH$_2$ In the same manner as Example 34-e), 0.80 g. of Z-Arg(NO$_2$)-Gly-Phe-Phe-NH$_2$ was treated with HBr-acetic acid and dissolved in 10 ml. of DMF. The solution was neutralized with triethylamine. On the other hand, 0.32 g. of Z-ε-Acap-OH and 0.24 g. of HONB were dissolved in 5 ml. of tetrahydrofuran and, while cooling with ice, 0.27 g. of DCC was added. The mixture was stirred for 3 hours and the formed dicyclohexylurea was filtered off and the filtrate was added to the above amine component [H-Arg(NO$_2$)-Gly-Phe-Phe-NH$_2$]. The mixture was stirred overnight. The solvent was distilled off under reduced pressure and water was added. The resltant powder was recovered by filtration and dried well. It was then washed with ethyl acetate and recrystallized from DMF-ethyl acetate. Yield: 0.49 g. (55 %); melting point: 102–104° C; $[\alpha]_D^{21} -20.0°$ (c=1.0%, DMF); elemental analysis calcd. for $C_{39}H_{50}O_9N_{10} \cdot \frac{1}{2}H_2O$ : C, 57.69; H, 6.33; N, 17.25; found: C, 57,86; H, 6.40; N, 16.76.

(b) Production of ε-Acap-Arg-Gly-Phe-Phe-NH$_2$

In 30 ml. of acetic acid was dissolved 400 mg. of Z-ε-Acap-Arg(NO$_2$)-Gly-Phe-Phe-NH$_2$ and, with Pd as a catalyst, catalytic reduction was carried out for 7 hours. The catalyst was filtered off and the solvent was distilled off under reduced pressure. The residue was applied on a column (1.8 cm × 10 cm) of carboxymethylsephadex, and elution was carried out by the linear gradient method from 0.1N aqueous ammonium acetate (500 ml.) through 1N aqueous ammonium acetate (500 ml.). The fractions from 250 ml. to 330 ml. were pooled and lyophilized. Yield 200 mg. (51%); $[\alpha]_D^{22} -9.9°$ (c=0.6%, water); elemental analysis: calcd. for $C_{32}H_{47}O_5N_9 \cdot 2C_2H_4O_2 \cdot 2H_2O$ : C, 54.46; H, 7.49; N, 15.88; found: C, 54.24; H, 7.26; N, 15.76; amino acid analysis: Arg 1.00(1), Gly 0.98(1), Phe 2.00(2), ε-Acap-(not determined); peptide content 79%.

EXAMPLE 38

Production of Lys-Arg-Gly-Phe-Phe-NH$_2$ (a) Production of di-Z-Lys-Arg(NO$_2$)-Gly-Phe-Phe-NH$_2$ In the same manner as Example 34-e), 0.80 g. of Z-ZArg(NO$_2$)-Gly-Phe-Phe-NH$_2$ was treated with HBr-acetic acid and, then, dissolved in 10 ml. of DMF. The solution was neutralized with triethylamine.

On the other hand, 0.54 g. of di-Z-Lys-OH and 0.26 g. of HONB were dissolved in 5 ml. of tetrahydrofuran and, while cooling with ice, 0.30 g. of DCC was added. The mixture was stirred for 4 hours and the formed dicyclohexylurea was filtered off. The filtrate was added to the above amine component (H-Arg(NO$_2$)-Gly-Phe-NH$_2$), followed by stirring overnight. The solvent was distilled off under reduced pressure and water was added to the residue. The resultant power was recoered by filtration and dried well. It was then washed with ethyl acetate and reprecipitated from DMF-ethyl acetate. Yield 0.82 g. (77%); melting point: 200°–204° C (decomp.) $[\alpha]_D^{23}$ −20.5°(c=1.1%, DMF); elemental analysis: calcd. for C$_{48}$H$_{59}$O$_{11}$N$_{11}$.$\frac{1}{2}$H$_2$O; C, 59.06; H, 6.20; N, 15.79; found: C, 59.04; H, 6.13; N, 15.78.

(b) Production of Lys-Arg-Gly-Phe-Phe-NH$_2$

In 30 ml. of acetic acid was dissolved 600 mg. of diZ-Lys-Arg(NO$_2$)-Gly-Phe-Phe-NH$_2$ and, with Pd as a catalyst, catalytic reducion was carried out for 6 hours. The catalyst was filtered off and the solvent was distilled off under reduced pressure. The residue was applied on a column (1.5 cm × 11 cm) of carboxymethyl-sephadex and elution was carried out by the linear gradient method from 0.1N aqueous ammonium acetate (700 ml.) through 1N aqueous ammonium acetate (700 ml.). The fractions from 650 ml. to 760 ml. were pooled and lyophilized. Yield 280 mg. (52%); $[\alpha]_D^{23}$ −4.3° (c=0.5%, water); elemental analysis: calcd. for C$_{32}$H$_{48}$O$_5$N$_{10}$.3C$_2$H$_4$O$_2$.2H$_2$O: C, 52.52; H, 7.42; N, 16.12; found: C, 52.64; H, 7.38; N, 16.42; amino acid analysis: Arg 1.06(1), Lys 1.09(1), Gly 1.00(1), Phe 1.97(2); peptide content 73%.

EXAMPLE 39

Production of α,γ-Dab-Arg-Gly-Phe-Phe-NH$_2$ (a) Production of di-Z-Dab-Arg(NO$_2$)-Gly-Phe-Phe-NH$_2$ In the same manner as Example 234-e), 0.80 g. of Z-Arg(NO$_2$)-Gly-Phe-Phe-NH$_2$ was treated with HBr-acetic acid and dissolved in 10 ml. of DMF. The solution was neutralized with triethylamine. On the other hand, 0.50 g. of di-Z-α,γ-Dab-OH and 0.26 g. of HONB were dissolved in 5 ml. of tetrahydrofuran and, while cooling with ice, 0.30 g. of DCC was added. The mixture was stirred for 4 hours and the formed dicyclohexylurea was filtered off.

The filtrate was added to the above amine component (H-Arg(NO$_2$)-Gly-Phe-Phe-NH$_2$) and the mixture was stirred overnight. The solvent was distilled off under reduced pressure and water was added to the residue. The resultant powder was recovered by filtration and dried well. The powder was washed with ethyl acetate and reprecipitated from DMF-ethyl acetate. Yield 0.82 g. (78%); melting point: 184°–188° C; $[\alpha]_D^{23}$ −19.5°(c=1.1%, DMF); elemental analysis: calcd. for C$_{46}$H$_{55}$PO$_{11}$N$_{22}$.H$_2$O: C, 57.79; H, 6.01; N, 16.21; found: C, 57.95; H, 5.91; N, 16.19

(b) Production of α,γ-Dab-Arg-Gly-Phe-Phe-NH$_2$

In 30 ml. of acetic acid was dissolved 600 mg. of Di-Z-(α,γ-Dab-Arg(NO$_2$)-Gly-Phe-Phe-NH$_2$ and with Pd as a catalyst, catalytic reduction was carried out for 6 hours. The catalyst was filtered off and the solvent was distilled off under reduced pressure. The residue was applied on a column (1.5 cm × 13 cm) of carboxymethyl-sephadex and elution was carried out by the linear gradient method from 0.1N aqueous ammonium acetate (700 ml.) through 1N aqueous ammonium acetate (700 ml.). The fractions from 610 m . to 680 ml. were pooled and lyophilized. Yield 255 mg. (46%); $[\alpha]_D^{23}$ −12.5°(c=0.8%, water); elemental analysis: calcd. for C$_{30}$H$_{44}$O$_5$N$_{10}$.3C$_2$H$_4$O$_2$.3H$_2$O: C, 50.35; H, 7.28; N, 16.31; found: C, 50.59; H, 7.61; N, 16.93; amino acid analysis: Arg 1.00(1), Gly 1.00(1), Phe 1.98(2), α, -Dab 1.02(1); peptide content: 72%.

EXAMPLE 40

Production of Arg-Arg-Gly-Phe-Phe-NH$_2$ (a) Production of Z-Art(NO$_2$)-Arg(NO$_2$)-Gly-Phe-Phe-NH$_2$ In the same manner as Example 34-e), 0.80 g. of Z-Arg(NO$_2$)-Gly-Phe-Phe-NH$_2$ was treated with HBr-acetic acid and dissolved in 10 ml. of DMF. The solution was neutralized with triethylamine. On the other hand, 0.39 g. of Z-Arg(NO$_2$)-OH and 0.22 g. of 2,4-dinitrophenol were dissolved in 5 ml. of tetrahydrofuran and, while cooling with ice, 0.25 g. of DCC was added. The mixture was stirred for 2 hours and the formed dicyclohexylurea was filtered off. The filtrate was added to the above amine component [H-Arg(NO$_2$)-Gly-Phe-Phe-NH$_2$], followed by stirring overnight. The solvent was distilled off under reduced pressure and water was added to the residue. The oily product was washed well with water and reprecipitated from DMF-ethyl acetate. Yield 0.90 g. (89%); melting point: 89 -92° C; $[\alpha]_D^{23}$ −17.6°(c=1.0%, DMF); elemental analysis: calcd. for C$_{40}$H$_{52}$O$_{11}$N$_{14}$.H$_2$O: C, 51.05; H, 5.90; N, 21.25; found: C, 52.20; H, 6.16; N, 20.91

(b) Production of Arg-Arg-Gly-Phe-Phe-NH$_2$

In 40 ml. of acetic acid was dissolved 700 ml. of Z-Arg(NO$_2$)-Arg(NO$_2$)-Gly-Phe-Phe-NH$_2$ and, with Pd as a catalyst, catalytic reduction was carried out for 9 hours. The catalyst was filtered off and the solvent was distilled off under reduced pressure. The residue was applied on a column (3 cm × 18 cm ) of carboxymethyl-cellulose and elution was carried out from 0.005N aqueous ammonium acetate (1l.) through 0.3N aqueous ammonium acetate (1 l.). The fractions from 890 ml. to 1410 ml. were pooled and lyophilized. Yield 380 mg. (45%); $[E]_D^{22}$ +2.4° C(c=0.5%, 5% acetic acid); elemental analysis: calcd. for C$_{32}$H$_{48}$O$_5$N$_2$.3C$_2$H$_4$O$_2$.3/2H$_2$O: C, 51.40; H, 7.15; N, 18.93; found: C, 51.25; H, 7.29; N, 19.08; amino acid analysis: Arg 2.02(2), Gly 1.00(1), Phe 2.02(2); peptide content 73%.

EXAMPLE 41

Production of β-Ala-Arg-Gly-Phe-Phe-Tyr-NH$_2$ (a) Production of Z-β-Ala-Arg(NO$_2$)Gly-OEt To 26.3 g. of Z-Arg(NO$_2$)-Gly-OEt was added 130 ml. of 25% HBr-acetic acid and, after shaking at room temperature for 60 minutes, ethyl ether was added. The precipitate was recovered by filtration and dried over sodium hydroxide. The dried precipitate was then dissolved in 150 ml. of DMF and, after cooling with ice, the solution was neutralized with triethylamine. Therafter, 23.1 g. of Z-β-Ala-ONB was added and the mixture was stirred overnight. The solvent was distilled off under reduced pressure and the residue was dissolved in 300 ml. of ethyl aceteate containing a small amount of n-butanol. The solution was washed with water, a saturated aqueous solution of sodium hydrogen carbonate (100 ml. × 3) and a saturated aqueous solution of sodium chloride (100 ml. × 3), followed by drying over anhydrous sodium sulfate. The solvent was distilled off under reduced pressure and ethyl ether was added. The resultant powder was recovered by filtration and recrystallized from ethanol-ethyl acetate. Yield 22.9 g. (75%); melting point: 97°–99° C; $[\alpha]_D^{26.5} -11.2°$ (c=0.9%, DMF); elemental analysis: calcd. for $C_{21}H_{31}O_8N_7$: C, 49.50; H, 6.13; N, 19.25; found: C, 49.51; H, 6.06; N, 18.93.

(b) Production of Z-β-Ala-Arg(NO₂)-Gly-OH

In a mixture of 50 ml. acetone and 25 ml. of water was dissolved 12.1 g. of Z-β-Ala-Arg(NO₂)-Gly-OEt and, under cooling with ice and sodium chloride, 27.8 ml. of 1N aqueous sodium hydroxide solution was added dropwise over a period of 30 minutes. The mixture was stirred under the same conditions for 1 hour and for an additional 2 hours at room temperature and, after the addition of 3.8 ml. of 1N hydrochloric acid, the acetone was distilled off under reduced pressure. To the residue was added 50 ml. of water and the mixture was made acidic with 6N hydrochloric acid to yield an oily substance which was soon solidified.

The solid product thus obtained was collected by filtration. Yield 10.3 g. (86.0%); melting point: 101°–103° C; $[=]_D^{26.5} -10.2°$(c=1.0%, DMF); elemental analysis: calcd. for $C_{19}H_{27}O_8N_7 \cdot \frac{1}{2}H_2O$: C, 46.53; H, 5.75; N, 19.99; found: C, 46.28; H, 5.41; N, 20.01.

(c) Production of Z-Phe-Tyr-OMe

In 100 ml. of tetrahydrofuran was suspended 5.10 g. of Tyr-OMe·HCl and, after cooling with ice, the suspension was neutralized with 3.08 ml. of triethylamine. To this were added 5.99 g. of Z-Phe-OH, 3.94 g. of HONB and 4.54 g. of DCC, and the mixture was stirred overnight. The formed dicyclohexylurea was filtered off and the solvent was removed by evaporation under reduced pressure. The residue was dissolved in 200 ml. of ethyl acetate. The solution was washed with a saturated aqueous solution of sodium hydrogen carbonate (100 ml. × 3), with 1N hydrochloric acid (100 ml. × 3) and with water, followed by drying over amhydrous sodium sulfate. After the ethyl acetate was distilled off under reduced pressure, petroleum benzin was added to give a gelatinous residue which was recovered by filtration and reprecipitated from ethyl acetate-petroleum benzin. Yield 6.00 g. (63%); melting point: 132°–133° C; $[\alpha]_D^{26.5} -9.9°$ (c=1.0%, DMF); elemental analysis: calcd. for $C_{27}H_{28}O_6N_2$: C, 68.05; H, 5.92; N, 5.88; found: C, 68.07; H, 5.92; N, 5.95.

(d) Production of Z-Phe-Tyr-NH₂

In 40 ml. of methanol saturated with ammonia was dissolved 3.0 g. of Z-Phe-Tyr-OMe and the solution was stored in a sealed vessel for a week, whereupon needles separated. After the solvent was evaporated off under reduced pressure, ethyl ether was added and the resultant crystals were recovered by filtration and recrystallized from ethanol-water. Yield 2.61 g. (90%); melting point: 217°—218° C; $[\alpha]_D^{26.5} -28.6°$(c=1.0%, DMF); elemental analysis: calcd. for $C_{26}H_{27}O_5N_3$: C, 67.66; H, 5.90; N, 9.11; found: C, 67.45; H, 5.88; N, 9.05.

(e) Production of Z-Phe-Phe-Tyr-NH₂

To 1.15 g. of Z-Phe-Tur-NH₂ was added a small amount of anisole, followed by the addition of 11 ml. of 25% HBr-acetic acid. After shaking at room temperature for 40 minutes, ethyl ether was added. The resultant precipitate was recovered by filtration and dried over sodium hydroxide. On the other hand, 0.67 g. of Z-Phe-OH and 0.45 g. of HONB were dissolved in 5 ml. of tetrahydrofuran and, while cooling with ice, 0.52 g. of DCC was added. The mixture was stirred for 4 hours and the formed dicyclohexylurea was filtered off. The above amine component (H-Phe-Tyr-NH₂) was dissolved in 10 ml. of DMF and the solution was neutralized with triethylamine. To this solution was added the above active ester solution and the mixture was stirred overnight. The solvent was distilled off under reduced pressure and water was added. The resultant crystals were recovered by filtration, washed with ethyl acetate and recrystallized from DMF-ethyl acetate. Yield 1.01 g. (74%); melting point: 218°–221° C (decomp.); $[\alpha]_D^{26.5} -27.7°$(c=1.0%, DMF); elemental analysis: calcd. for $C_{35}H_{36}O_6N_4$: C, 69.06; H, 5.96; N, 9.21; found: C, 69.01; H, 6.02; N, 9.23.

(f) Production of Z-β-Ala-Arg(NO₂)-Gly-Phe-Phe-Tyr-NH₂

In a mixture of 30 ml. of methanol and 20 ml. of DMF was suspended 0.91 g. of Z-Phe-Phe-Tyr-NH₂ and catalytic reduction as carried out for 7 hours. The methanol was distilled off under reduced pressure. On the other hand, 0.72 g. of Z-β-Ala-Arg(NO₂)-Gly-OH and 0.32 g. of HONB were dissolved in 5 ml. of DMF and, while cooling with ice, 0.37 g. of DCC was added. The mixture was stirred for 6 hours and the formed diocyclohexylurea was filtered off. The filtrate was dded to the above amine component (H-Phe-Phe-Tyr-NH₂), followed by stirring overnight. The solvent was evaporated off under reduced pressure to give a solid which was triturated with water. The resultant powder was recovered by filtration and reprecipitated from DMF-ethyl acetate. Yield 0.88 g. (62%); melting point: 174 -177° C; $[\alpha]_D^{26.5} -15.0°$(c=1.0%. DMF); elemental analysis: calcd. for $C_{44}H_{55}O_{11}N_{11} \cdot H_2O$: C, 57.79; H, 6.01; N, 16.12; found: C, 58.54; H, 6.18; N, 16.21.

(g) Production of β-Ala-Arg-Gly-Phe-Phe-Tyr-NH₂

In 30 ml. of acetic acid was dissolved 740 mg. of Z-β-Ala-Arg(NO₂)-Gly-Phe-Phe-Tyr-NH₂ and, with Pd as a catalyst, catalytic reduction was carried out for 7 hours. The catalyst was filtered off and the solvent was distilled off under reduced pressure. The residue was applied on a column (1.6 cm × 15 cm) of carboxymethyl-sephadex and elution was carried out by the linear gradient method from 0.005N aqueous ammonium acetate (700 ml.) to 1N aqueous ammonium acetate (700 ml.). The fractions from 580 ml. to 780 ml. were pooled and lyophilized. Yield 540 mg.(75%); $[\alpha]_D^{26} -20.0°$ (c=0.5%, water); elemental analysis: calcd. for $C_{38}H_{50}O_7N_{10} \cdot 2C_2H_4O_2 \cdot 3H_2O$: C, 54.06; H, 6.91; N, 15.01; found: C, 54.20; H, 6.50; N, 14.99; amino acid analysis: Arg 0.95(1), Gly 1.05(1), Tyr 1.00(1), Phe 2.00(2); peptide content 74%.

(h) Production of β-Ala-Arg-Gly-Phe-Phe-Tyr-NH₂ di-citrate The acetate, β-Ala-Arg-Gly-Phe-Phe-Tyr-NH₂ diacetate trihydrate, (9.33 g) was dissolved in 20 ml. of water, and to this was added 2.2 g. of citric acid monohydrate with stirring. The formed crystalline precipitate was collected by filtration and washed with smal volume of cold water to give 10.4 g of the corresponding di-citrate. $[\alpha]_D^{23} -19.6°$ (c=1.0 in water) Elemental analysis Calcd. for $C_{38}H_{50}O_7N_{10} \cdot 2\ C_6H_8O_7$: C, 52.54; H, 5.82; N, 12.25. Found: C, 52.28; H, 5.87; N, 12.46.

EXAMPLE 42

Production of γ-Abu-Arg-Gl-Phe-Phe-Tyr-$NH_2$ (a) Production of Z-γ-Abu-Arg($NO_2$)-Gly-OEt To 4.38 g. of Z-Arg($NO_2$0-Gly-OEt was added 40 ml. of 25% HBr-acetic acid and, after shaking at room temperature for 30 minutes, ethyl ether was added. The resultant precpitate was recovered by filtration and dried over sodium hydroxide.

It was then dissolved in 30 ml. of DMF and, after cooling with ice, the solution was neutralized with triethylamine. To this solution was added 4.16 g. of Z-γ-Abu-ONB and the mixture was stirred overnight. The solvent was distilled off under reduced pressure and water was added to the residue. The water was removed by decantation. Ethyl ether was added to the residue, whereby the latter was solidified. It was then recovered by filtration and reprecipitated from acetonitrile. Yield 2.5 g. (48%); melting point: 60°-62° C $[\alpha]_D^{21} - 11.1°(c=1.0$, DMF); elemental analysis: calcd. for $C_{22}H_{33}O_8N_7$: C, 50.47; H, 6.35; N, 18.73; found: C, 50.12; H, 6.51; N, 18.73.

(b) Production of Z-γ-Abu-Arg($NO_2$)-Gly-OH

In 20 ml. of acetone was dissolved 2.0 g. of Z-γ-Abu-Arg($NO_2$)-Gly-OEt and, while cooling with ice, 5.7 ml. of 1N aqueous sodium hydroxide solution was added. The mixture was stirred at room temperature for 2 hours. Following the addition of 6 ml. of 1N hydrochloric acid, the acetone was distilled off under reduced pressure. The resulting crystals were recovered by filtration and recrystallized from ethanol-water. Yield: 1.86 g. (98%); melting point: 113°-115° C; $[\alpha]_D^{21} - 20.0°$ (c=1.1%, DMF); elemental analysis; calcd. for $C_{20}H_{29}O_8N_7 \cdot H_2O$: C, 46.78; H, 6.09; N, 19.10; found: C, 57.12; H, 5.90; N, 19.23

(c) Production of Z-γ-Abu-Arg($NO_2$)-Gly-Phe-Phe-Tyr-$NH_2$

To 1.34 g. of Z-Phe-Phe-Tyr-$NH_2$ was added a small amount of anisole, followed by addition of 13 ml. of 25% HBr-acetic acid.

After shaking at room temperature for 45 minutes, ethyl ether was added and the resultant precipitate was recovered by filtration and dried over sodium hydroxide. On the other hand, 0.99 g. of Z-γ-Abu-Arg($NO_2$)-Gly-OH and 0.43 g. of HONB were dissolved in 5 ml. of DMF and, under cooling with ice, 0.50 g. of DCC was added. The mixture was stirred for 6 hours and the dicyclohexylurea was filtered off. The above amine component ([H-Phe-Phe-Tyr-$NH_2$] was dissolved in 10 ml. of DMF and the solution was neutralized with triethylamine. To this solution was added the above active ester solution and the mixture was stirred overnight. The solvent was distilled off under reduced pressure and water was added. The resultant powder was recovered by filtration, washed with ethyl acetate and reprecipitated from DMF-ethyl acetate. Yield 1.12 g. (58%), melting point: 139.5–141° C; $[\alpha]_D^{21} - 13.2°(c=1.4\%$, DMF); elemental analysis: calcd. for $C_{47}H_{57}O_{11}N_{11} \cdot H_2O$: C, 58.19; H, 6.13; N, 15.89; found: C, 57.76; H, 6.43; N, 15.91.

(d) Production of γ-Abu-Arg-Gly-Phe-Phe-Tyr-$NH_2$

In 30 ml. of acetic acid was dissolved 800 mg. of Z-γ-Abu-Arg($NO_2$)-Gly-Phe-Phe-Tyr-$NH_2$ and, with Pd as a catalyst, catalytic reduction was carried out for 14 hours. The catalyst was filtered off and the solvent was removed by distillation under reduced pressure. The residue was applied on a column (1.5 cm × 10 cm) of carboxymethyl-sephadex and elution was carried out by the gradient elution method from 0.1N aqueous ammonium acetae (700 ml.) through 1N aqueous ammonium acetate (700 ml.). The fractions from 410 ml. to 600 ml. were pooled and lyophilized. Yield 412 mg. (52%); $[\alpha]_D^{22} - 18.1°$ (c=0.5%), water); elemental analysis: calcd. for $C_{39}H_{52}O_7N_{10} \cdot 2C_2H_4O_2 \cdot 4H_2O$: C, 54.02; H, 7.10; N, 14.52; found: C, 54.08; H, 7.07; N, 14.60; amino acid analysis: Arg 0.96(1), Gly 1.00(1), Tyr 0.97(1), Phe 2.10(2); peptide content 84%.

EXAMPLE 43

Production of ε-Acap-Arg-Gly-Phe-Phe-Tyr-$NH_2$ (a) Production of Z-ε-Acap-Arg($NO_2$)-Gly-OEt To 2.41 g. of Z-Arg($NO_2$)-Gly-OET was added 12 ml. of 25% HBr-acetic acid and, after shaking at room temperature for 40 minutes, ethyl ether was added. The resultant precipitate was recovered by filtration and dried over sodium hydroxide.

On the other hand, 1.33 g. of Z-ε-Acap-OH and 0.99 g. of HONB were dissolved in 5 ml. of tetrahydrofuran and, while cooling with ice, 1.14 g. of DCC was added.

The mixture was stirred for 4 hours and the formed dicyclohexylurea was filtered off. The above amine component was dissolved in 10 ml. of DMF and, after the solution was neutralized with triethylamine, the above active ester solution was added. The mixture was stirred overnight and the solvent was distilled off under reduced pressure. The residue was dissolved in 50 ml. of ethyl acetate and the solution was washed with water, with a saturated aqueous solution of sodium hydrogen carbonate (50 ml. × 2) and with water, followed by drying over anhydrous sodium carbonate. The solvent was distilled off under reduced pressure and petroleum benzin was added. The resultant crystals were recrystallized from water-ethanol-ethyl acetate. Yield 2.1 g. (76%); melting point: 85–87° C; $[\alpha]_D^{24} - 11.9°(c=1.0\%$, DMF); elemental analysis; calcd. for $C_{24}H_{37}O_8N_7$: C, 52.26; H, 6.76; N, 17.78; found: C, 52.43; H, 6.64; N, 17.76.

(b) Production of Z-ε-Acap-Arg($NO_2$)-Gly-OH

In 10 ml. of acetone was dissolved 1.8 g. of Z-ε-Acap-Arg($NO_2$)-Gly-OEt and, while cooling with ice, 2.9 ml. of 2N aqueous sodium hydroxide solution was added. The mixture was stirred at room temperature for 2 hours. Following the addition of 2.5 ml. of 1N hydrochloric acid, the acetone was distilled off under reduced pressure. To the residue was added 10 ml. of water and the insolubles were filtered off. The filtrate was made acidic with 1N hydrochloric acid, whereupon crystals separated. These crystals were recovered by filtration. Yield 1.59 g. (93%); melting point: 97.5–99° C; $[\alpha]_D^{24} - 10.7°(c=1.0\%$, DMF); elemental analysis: calcd. for $C_{22}H_{33}O_8N_7 \cdot H_2O$: C, 48.79; H, 6.52; N, 18.10; found: C, 48.50; H, 6.28; N, 18.23

(c) Production of Z-ε-Acap-Arg($NO_2$)-Gly-Phe-Phe-Tyr-$NH_2$

To 1.22 g. of Z-Phe-Phe-Tyr-$NH_2$ was added a small amount of anisole, followed by addition of 10 ml. of 25% HBr-acetic acid. The mixture was shaken at room temperature for 40 minutes and ethyl ether was added. The precipitate was recovered by filtration and dried over sodium hydroxide. On the other hand, 1.05 g. of Z-ε-Acap-Arg($NO_2$)-Gly-OH and 0.36 g. of HONB were dissolved in 10 ml. of DMF and, under cooling with water, 0.42g. of DCC was added. The mixture was stirred for 6 hours and the byproduct dicyclohexylurea was filtered off. The above amine component was dissolved in 10 ml. of DMF and the solution was neutralized with triethylamine.

To this solution was added the above active ester solution and the mixture was stirred overnight. The solvent was distilled off under reduced pressure and water was added. The resultant powder was recovered by filtration, washed with ethyl acetate and reprecipitated from DMF-ethyl acetate. Yield 1.01 g. (57%); melting point: 149°–151° C; $[\alpha]_D^{26} -12.9°(c=1.1\%, DMF)$; elemental analysis: calcd. for $C_{57}H_{67}O_{13}N_{11}.1/2H_2O$: C, 59.50; H, 6.32; N, 15.58; found: C, 59.63; H, 6.43; N, 15.03.

(d) Production of ε-Acap-Arg-Gly-Phe-Phe-Tyr-NH$_2$

In 40 ml. of acetic acid was dissolved 700 mg. of Z-ε-Acap-Arg(NO$_2$)-Gly-Phe-Phe-Tyr-NH$_2$ and, with Pd as a catalyst, catalytic reduction was carried out for 14 hours. The catalyst was filtered off and the solvent was removed by distillation under reduced pressure. The residue was applied on a column of carboxymethylsephadex (1.8 cm × 12 cm) and elution was carried out by the linear gradient method from 0.1N aqueous ammonium acetate (700 ml.) to 1N aqueous ammonium acetate (700 ml.) to 1N aqueous ammonium acetate (700 ml.). The fractions from 430 ml. to 550 ml. were pooled and lyophilized. Yield 430 mg.(62%); $[\alpha]_D^{26} -13.2°(c=0.5\%, water)$: elemental analysis: calcd. for $C_{41}H_{56}O_7N_{10}.2C_2H_4O_2.3H_2O$: C, 55.43; H, 7.24; N, 14.37; found: C, 55.48; H, 7.39; N, 14.47; amino acid analysis: Arg 1.00(1), Gly 1.00(1), Tyr 1.00(1), Phe 2.07(2); peptide content 84%.

EXAMPLE 44

Production of Lys-Arg-Gly-Phe-Phe-Tyr-NH$_2$ (a) Production of di-Z-Lys-Arg(NO$_2$)-Gly-OEt Using 2.07 g. of di-Z-Lys-OH, exactly the same procedure as Example 43-a) was followed to obtain the desired compound as gel. Reprecipitation from water-ethanol-ethyl acetate yielded 2.57 g. (73%); melting point: 161°–162° C; $[\alpha]_D^{24} -11.9°(c=1.0\%, DMF)$; elemental analysis: calcd. for $C_{32}H_{44}O_{10}N_8$: C, 54.85; H, 6.33; N, 15.99; found: C, 54.45; H, 6.05; N, 15.99.

(b) Production of di-Z-Lys-Arg(NO$_2$)-Gly-OH

In 10 ml. of acetone was dissolved 2.0 g. of di-Z-Lys-Arg(NO$_2$)-Gly-OEt and, while cooling with ice, 2.1 ml. of 2N aqueous sodium hydroxide solution was added. The mixture was stirred at room temperature for 2 hours. Following the addition of 1.4 ml. of 1N hydrochloric acid, the acetone was distilled off under reduced pressure. The residue was diluted with 10 ml. of water and the insolubles were filtered off. The solution was then made acidic with 1N hydrochloric acid and the resultant gelationous precipitate was recovered by filtration. Yield 1.78 g. (93%); melting point: 131°–132.5° C; $[\alpha]_D^{24} -10.5°(c=1.0, DMF)$; elemental analysis: calcd. for $C_{30}H_{40}O_{10}N_8.3/2H_2O$: C, 51.49; H, 6.20; N, 16.02; found: C, 51.43; H, 5.92; N, 16.23

(c) Production of di-Z-Lys-Arg(NO$_2$)-Gly-Phe-Phe-Tyr-NH$_2$

Using 1.21 g. of di-Z-Lys-Arg(NO$_2$)-Gly-OH, exactly the same procedure as Example 43-c) was followed to obtain the desired compound as gel. Yield 1.21 g. (58%); melting point: 199°–203° C; $[\alpha]_D^{24} -13.3°(c=1.0, DMF)$; elemental analysis: calcd. for $C_{57}H_{68}O_{13}N.2H_2O$: C, 58.75; H, 6.23; N, 14.42; found: C, 58.70; H, 6.26; N, 14.72.

(d) Production of Lys-Arg-Gly-Phe-Phe-Tyr-NH$_2$

In 30 ml. of acetic acid was dissolved 1.00 g. of di-Z-Lys-Arg(NO$_2$)-Gly-Phe-Phe-Tyr-NH$_2$ and, with Pd as a catalyst, catalytic reduction was carried out for 20 hours. The catalyst was filtered off and the solvent was removed by distillation under reduced pressure. The residue was applied on a column (1.8 cm × 10 cm). of carboxymethylsephadex. Elution was carried out by the linear gradient method from 0.1N aqeous acetate (500 ml.) through 1N aqueous ammonium acetate (500 ml.) and the fractions from 650 ml. to 890 ml. were pooled and lyophilized. Yield 468 mg. (50%); $[\alpha]_D^{26} -10.6°(c=0.5\%;$ water); elemental analysis: calcd. for $C_{41}H_{57}O_7N_{11}.3C_2H_4O_2.4H_2O$: C, 52.84; H, 7.27; N, 14.43; found: C, 52.70; H, 7.31; N, 14.72; amino acid analysis: Arg 1.00(1). Lys 0.94(1), Gly 1.00(1), Tyr 1.00(1), Phe 2.06(2); peptide content: 82%.

EXAMPLE 45

Production of α, γ-Dab-Arg-Gly-Phe-Phe-Tyr-NH$_2$ (a) Production of di-Z-α,γ-Dab-Arg(NO$_2$)-Gly-OEt In 40 ml. of ethyl ether was suspended 2.84 g. of di-Zα,γ-Dab-OH.DCHA ("DCHA" is an abbreviation for dicyclohexylamine) and the suspension was shaken with 0.5N sulfuric acid. The ethereal layer was washed with water and dried over anhydrous sodium sulfate. The solvent was distilled off and exactly the same procedure as Example 43-a) was followed to obtain the desired compound as gel. It was reprecipitated from water-ethanol-ethyl acetate. Yield 2.36 g. (70%); melting point: 153°–156° C; $[\alpha]_D^{24} -9.4°(c=1.0\%, DMF)$, elemental analysis: calcd. for $C_{30}H_{40}O_{10}N_8$: C, 53.56; H, 5.99; N, 16.66; found: C, 53.26; H, 5,84; N, 16.24.

(b) Production of di-Z-α,γ-Dab-Arg(NO$_2$)-Gly-OH

In 10 ml. of acetone was dissolved 2.0 g. of di-Z-α, γ-Dab-Arg-(NO$_2$)-Gly-Oet and, under cooling with ice, 2.97 ml. of 2N aqueous sodium hydroxide was added dropwise. The mixture was stirred under the same conditions for 1 hour and 3 ml. of 1N hydrochloric acid was added. The acetone was distilled off under reduced pressure and 10 ml. of water was added. The insolubles were filtered off and the filtrate was made acidic with 1N hydrochloric acid. The resultant gelatinous precipitate was recovered by filtration. Yield 1.67 g. (90%); melting point: 112°–113° C; $[\alpha]_D^{26} -8.3°(c=1.1\%, DMF)$; elemental analysis: calcd. for $C_{28}H_{36}O_{10}N_8.H_2O$: C, 50.55; H, 5.76; N, 16.89; found: C, 50.53; H, 5.59; N, 17.19.

(c) Production of di-Z-α, γ-Dab-Arg(NO$_2$)-Gly-Phe-Phe-Tyr-NH$_2$

Using 1.12g. of di-Z-α,γ-Dab-Arg-(NO$_2$)-Gly-Oh, exactly the same procedure as Example 43-c) was followed to obtain the desired compound as gel. Yield 1.02 g. (51%); melting point: 191°–195° C; $[\alpha]_D^{26} -14.0°(c=0.9\%, DMF)$; elemental analysis: calcd. for $C_{55}H_{65}O_{13}N_{12}.H_2O$ : C, 59.02; H, 5.95; N, 15.02; found: C, 59.13; H, 6.14; N, 15.46

(d) Production of α,γ-Dab-Arg-Gly-Phe-Phe-Tyr-NH$_2$

In 30 ml. of acetic acid was dissolved 600 mg. of di-Z-α,γ-Dab-Arg(NO$_2$)-Gly-Phe-Phe-Tyr-NH$_2$ and, with Pd as a catalyst, catalytic reduction was carried out for 12 hours. The catalyst was filtered off and the solvent was removed by evaporation under reduced pressure. The residue was applied on a column (1.8 cm × 10 cm) of carboxymethylsephadex and elution was carried out by the linear gradient method from 0.1N aqueous ammonia acetate (500 ml.) through 1N aqueous ammonia acetate (500 ml.). The fractions from 490 ml. to 620 ml. were pooled and lyophilized. Yield 241 mg. (43%); $[\alpha]_D^{26} -17.9°(c=0.6\%,$ water); elemental analysis: calcd. for $C_{39}H_{53}O_7N_{11}.3C_2H_4O_2.4H_2O$ : C, 51.96; H, 7.08; N, 14.82; found: C, 52.12; H, 6.99; N, 15.31; amino acid analysis: Arg 1.00(1), Dab 1.04(1), Gly 1.09(1), Tyr 1.02(1), Phe 2.13(2); peptide content 79%.

In all the claims, where there are optical isomers with respect to amino acids, the amino acids means each of the optical isomers and racemic compounds unless otherwise specifically designated.

What we claim is:

1. A composition for the treatment of diabetes or hyperchlolesteremia which comprises a medicinally effective amount of an active ingredient of the formula $$R_1-Arg-R_2-Phe-Phe-R_3 \qquad (I)$$

wherein $R_1$ is hydrogen, or a basic or neutral amino acid residue having not more than 10 carbon atoms, $R_2$ is a neutral amino acid residue having not more than 10 carbon atoms and $R_3$ is $NH_2$, Tyr-$NH_2$, a residue of $Tyr^1$-peptide consisting of 2 to 5 amino acid residues, each of the amino acid residues having 2 to 10 carbon atoms, or $R_3$ is a residue of an amide of the $Tyr^1$-peptide, provided that when $R_1$ is hydrogen, $R_2$ is Pro and that when any of the amino acid residues constituting the compound of the formula (I) is an optical isomer, the amino acid residue is in L-configuration, in admixture with a pharmaceutically effective carrier therefor.

2. A composition as claimed in claim 1, wherein $R_1$ is a residue of the basic or neutral amino acid having no more than 10 carbon atoms, except for neutral α-amino acid, $R_2$ is Gly and $R_3$ is $NH_2$ or Tyr-$NH_2$, provided that when any of the amino acid residues constituting the compound of the formula (I) is an optical isomer, the amino acid residue is in L-configuration.

3. A composition as claimed in claim 1, wherein $R_2$ is a neutral amino acid residue having not less than 3 carbon atoms, provided that when any of the amino acid residues constituting the compound of the formula (I) is an optical isomer, the amino acid residue is in L-configuration.

4. A composition as claimed in claim 1, wherein $R_1$ is β-Ala.

5. A composition as claimed in claim 1, wherein $R_2$ is Gly.

6. A composition as claimed in claim 1, wherein $R_2$ is L-Pro.

7. A composition as claimed in claim 1, wherein $R_3$ is $NH_2$.

8. A composition as claimed in claim 1, wherein $R_3$ is L-Tyr-$NH_2$.

9. A composition as claimed in claim 1, wherein $R_2$ is Gly and $R_3$ is L-Tyr-$NH_2$.

10. A composition as claimed in claim 1, wherein $R_2$ is L-Pro and $R_3$ is L-Tyr-$NH_2$.

11. A composition as claimed in claim 1, wherein $R_1$ is β-Ala and $R_2$ is Gly.

12. A composition as claimed in claim 1, wherein $R_1$ is β-Ala and $R_2$ is L-Pro.

13. A composition as claimed in claim 1, wherein $R_1$ is β-Ala and $R_3$ is $NH_2$.

14. A composition as claimed in claim 1, wherein $R_1$ is β-Ala and $R_3$ is L-Tyr-$NH_2$.

15. A composition as claimed in claim 1, wherein the compound is of the formula

β-Ala-L-Arg-Gly-L-Phe-L-Phe-L-Tyr-$NH_2$.

16. A composition as claimed in claim 1, wherein the compound is of the formula

β-Ala-L-Arg-L-Pro-L-Phe-L-Phe-L-Tyr-$NH_2$.

17. A composition as claimed in claim 1, wherein the compound is of the formula

γ-Abu-L-Arg-L-Pro-L-Phe-L-Phe-L-Tyr-$NH_2$.

18. A composition as claimed in claim 1, wherein the compound is of the formula

ε-Acap-L-Arg-L-Pro-L-Phe-L-Phe-L-Tyr-$NH_2$.

19. A composition as claimed in claim 1, wherein the compound is of the formula

β-Ala-L-Arg-Gly-L-Phe-L-Phe-L-Tyr-Ala-Gly-$NH_2$.

20. A composition as claimed in claim 1, wherein the compound is of the formula

β-Ala-L-Arg-Gly-L-Phe-L-Phe-L-Tyr-L-Thr-L-Pro-L-Lys-L-Ala-OH.

21. A composition as claimed in claim 1, wherein the compound is of the formula

β-Ala-L-Arg-L-Leu-L-Phe-L-Phe-L-Tyr-Gly-$NH_2$.

* * * * *